United States Patent [19]

Lee et al.

[11] Patent Number: 5,589,336
[45] Date of Patent: Dec. 31, 1996

[54] DIAGNOSTIC METHOD AND KIT FOR DETERMINING KELL BLOOD GROUP GENOTYPE

[75] Inventors: Soohee Lee, Cliffside Park, N.J.; Colvin Redman, Long Island, N.Y.

[73] Assignee: New York Blood Center, New York, N.Y.

[21] Appl. No.: 337,268

[22] Filed: Nov. 10, 1994

[51] Int. Cl.$^6$ ............... C12Q 1/68; C12P 19/34; C07H 21/02; C07H 21/04
[52] U.S. Cl. ............... 435/6; 435/91.2; 435/7.1; 435/7.2; 536/23.1; 536/24.3; 536/24.31; 536/24.33; 424/188.1; 530/324; 530/388.1
[58] Field of Search ............... 538/23.1, 24.3–24.33; 530/300, 324; 424/188.1; 435/7.1–7.2, 6, 91.2

[56] References Cited

U.S. PATENT DOCUMENTS

| | | | |
|---|---|---|---|
| 4,148,607 | 4/1979 | Bernoco et al. | 435/7.1 |
| 4,358,436 | 11/1982 | Graham et al. | 435/7.25 |
| 4,403,042 | 9/1983 | Henry et al. | 435/7.24 |
| 4,560,647 | 12/1985 | Stocker | 435/5 |
| 5,213,963 | 5/1993 | Uthemann | 435/7.25 |
| 5,302,512 | 4/1994 | Pernelle | 435/7.25 |
| 5,324,479 | 6/1994 | Naldoni et al. | 422/63 |

OTHER PUBLICATIONS

Berkowitz et al., Death in Utero Due to Kell Sensitization Without Excessive Elevation of the $\Delta OD_{450}$ Value in Amniotic Fluid, *Obstetrics & Gynecology*, 60(6): 746–749 (1982).
Bowman et al., Maternal Kell Blood Group Alloimmunization, *Obstetrics & Gynecology*, 79(2): 239–244 (1992).
Chang et al., Molecular Characterization of Erythrocyte Glycophorin C Variants, *The American Society of Hematology—Blood*, 77(3): 644–648 (1991).
Constantine, Anti–Kell in Pregnancy, *Lancet*, 338: 198 (1991).
Constantine et al., Anti–Kell in Pregnancy, *British Journal of Obstetrics and Gynaecology*, 98: 943–944 (1991).
Cullen, Erythroblastosis Fetalis Produced by Kell Immunization: Dental Findings, *Pediatric Dentistry*, 12(6): 393–396 (1990).
Duguid et al., Haemolytic Disease of the Newborn Due to Anti–K, *Vox Sang*, 58: 69 (1990).
Gusdon, Jr. et al., Amniotic Fluid Analysis in Erythroblastosis Secondary to Kell Immunization, *Obstetrics and Gynecology*, 33(3): 432–434 (1969).
Hardie et al., Neuroacanthocytosis—A Clinical, Haematological and Pathological Study of 19 Cases, *Oxford University Press—Brain*, 114: 13–44 (1991).
Jaber et al., Characterization of Murine Monoclonal Antibodies Directed Against the Kell Blood Group Glycoprotein, *British Journal of Haematology*, 79: 311–315 (1991).
Jaber et al., Characterization of the Blood Group Kell (K1) Antigen with a Human Monoclonal Antibody, *Blood*, 73(6): 1597–1602 (1989).

(List continued on next page.)

*Primary Examiner*—W. Gary Jones
*Assistant Examiner*—Dianne Rees
*Attorney, Agent, or Firm*—Hoffmann & Baron

[57] ABSTRACT

The invention provides a diagnostic method of determining Kell genotype by the identification of the molecular basis of a Kell polymorphism. Specifically, the invention provides a method for determining K1/K2 genotype with great accuracy, overcoming problems associated with traditional serological typing methods. The diagnostic method of the invention preferably employs amplification of K1/K2 nucleic acid sequences, and optionally employs differential cleavage of K1- and K2-specific nucleic acid sequences by a restriction enzyme. Also provided are nucleic acid oligomers useful as probes or primers for the method of the invention. Furthermore, diagnostic kits for the determination of Kell genotype are provided.

57 Claims, 26 Drawing Sheets

K2      (SEQ ID NO:57)
185     Trp Thr Ser Leu Asn Phe <u>Asn Arg Thr</u> Leu Arg Leu Leu Met Ser        199
        TGG ACT TCC TTA AAC TTT AAC CGA ACG CTG AGA CTT CTG ATG AGT

K1      (SEQ ID NO:58)
        TGG ACT TCC TTA AAC TTT AAC CGA ATG CTG AGA CTT CTG ATG AGT
        Trp Thr Ser Leu Asn Phe <u>Asn Arg Met</u> Leu Arg Leu Leu Met Ser

OTHER PUBLICATIONS

Lee et al., The Human Kell Blood Group Gene Maps to Chromosome 7q33 and Its Expression is Restricted to Erythroid Cells, *The American Society of Hematology—Blood*, 81(10): 2804–2809 (1993).

Lee et al., Molecular Cloning and Primary Structure of Kell Blood Group Protein, *Proc. Natl. Acad. Sci. USA*, 88: 6353–6357 (1991).

Leggat et al., Anti–Kell in Pregnancy, *British Journal of Obstetrics and Gynaecology*, 98: 162–165 (1991).

Marsh et al., Recent Developments in the Kell Blood Group System, *Transfusion Medicine Reviews*, 1(1): 4–20 (1987).

Marsh et al., The Kell Blood Group System: A Review, *Transfusion*, 30(2): 158–167 (1990).

Mayne et al., The Significance of Anti–Kell Sensitization in Pregnancy, *Clin. Lab. Haemat.*, 12: 379–385 (1990).

Moncharmont et al., A Case of Hemolytic Disease of the Newborn Infant Due To Anti–K (Cellano), *Acta Haematol*, 85: 45–46 (1991).

Murphy et al., Regional Chromosomal Assignment of the Kell Blood Group Locus (KEL) to Chromosome 7q33–q35 by Fluorescene In Situ Hybridization: Evidence for the Polypeptide Nature of Antigenic Variation, *Human Genetics*, 91: 585–588 (1993).

Parsons et al., Monoclonal Antibodies Against Kell Glycoprotein: Serology, Immunochemistry and Quantification of Antigen Sites, *Transfusion Medicine*, 3: 1–6 (1993).

Petty et al., Application of the Maiea Assay to the Kell Blood Group System, *Vox Sang*, 66: 216–224 (1994).

Purohit et al., The Kell Blood Group Locus is Close to the Cystic Fibrosis Locus on Chromosome 7, *Human Genetics*, 89: 457–458 (1992).

Redman et al., Kell Blood Group Antigens Are Part of a 93,000–Dalton Red Cell Membrane Protein*, *The Journal of Biological Chemistry*, 261(20): 9521–9525 (1986).

Redman et al., Comparison of Human and Chimpanzee Kell Blood Group Systems, *Transfusion*, 29(6): 486–490 (1989).

Redman et al., Isolation of Kell–Active Protein From the Red Cell Membrane, *Transfusion*, 24(2): 176–178 (1984).

Redman et al., The Kell Antigens and McLeod Red Cells: 53–69.

Redman et al., The Kell Blood Group System and the McLeod Phenotype, *Seminars in Hematology*, 30(3): 209–218 (1993).

Telen et al., Erythrocyte Webb–Type Glycophorin C Variant Lacks N–Glycosylation Due to an Asparagine to Serine Substitution, *American Journal of Hematology*, 37: 51–52 (1991).

Vaughn et al., Anti–Kell in Pregnancy, *Lancet*, 338: 199 (1991).

Wallas et al., Isolation of a Kell–Reactive Protein from Red Cell Membrane, *Transfusion*, 26(2): 173–175 (1986).

Zelinski et al., Genetic Linkage Between The Kell Blood Group System and Prolactin–Inducible Protein Loci: Provisional Assignments of Kel to Chromosome 7, *Human Genetics*, 55: 137–140 (1991).

Zelinski, The Use of DNA Restriction Fragment Length Polymorphisms in Conjuction with Blood Group Serology, *Transfusion*, 31(8): 762–770 (1991).

Redman et al, JBC 261: 9521–9525 1986.

Redman et al, Transfusion 24: 176–178 1984.

Parsons et al, Transfusion Medicine 3: 1–6 1993.

Lee et al., PNAS 88: 6353–6357 1991.

Branch et al., "Disulfide bonds are a requirement of Kell and Cartwright ($Yt^a$) blood group antigen integrity," *Br. J. Haematol.* 54: 573–78 (1993).

Cherif–Zahar et al., "Organization of the gene (RHCE) encoding the human blood group RhCcEe antigens and characterization of the promoter region," *Genomics* 19: 68 (1994).

Furuhjelm et al., "The blood group antigen $U1^a$(Karhula)," *Vox Sang.* 15: 118–24 (1968).

Giblett et al., "A critique of the theoretical hazard of inter–vs. intra–racial transfusion," *Transfusion* 1: 233 (1961).

Giblett et al., "$Js^a$ a 'new' red cell antigen found in negroes: evidence for an eleventh blood group system," *Brit. J. Haematol.* 5: 319–26 (1959).

Marsh et al., "Blood groups of human red cells in clinical practice of blood transfusion," (Petz et al. eds.) pp. 79–130, Churchill–Livingstone, New York (1981).

FIG-2A

EXON 1 (SEQ ID NO:37)
1-123

```
                                               .....GAAGTGCCCCTTCTCCAGGATCAAGGAA   28
 29  CTGGGGGCGGGGGGTGTGTTTCCTGGACCCCAGTCCTCCGAATCAGCTCCTAGAGTGGAACC               87
                                                               Met
 88  AGGAAGGATTCTGGAGCCACAGAAGATAGACAG ATG gtaagtcccctttggagtcagagg......0.34kb
```

FIG-2B

EXON 2  (SEQ ID NO:38)
124-201

```
                                                               Glu Gly Gly      4
                           ctccttctctccctccactcacttcag GAA GGT GGG             132

Asp Gln Ser Glu Glu Pro Arg Glu Arg Ser Gln Ala Gly Gly                    19
  5  GAC CAA AGT GAG GAA CCG AGG GAA AGG AGC CAG GCA GGT GGA                   177

Met Gly Thr Leu Trp Ser Gln Glu
 20  ATG GGA ACT CTC TGG AGC CAA GAG gtaagtggcctcctctcctgggtct....0.29kb
178
```

FIG-2C

EXON 3
202-343 (SEQ ID NO:39)

```
                                    Ser Thr Pro Glu Glu Arg Leu      34
         tttcacctcttggttcctcccacag  AGC ACT CCA GAA GAG AGG CTG      222

35  Pro Val Glu Gly Ser Arg Pro Trp Ala Val Ala Arg Arg Val Leu     49
223  CCC GTG GAA GGG AGC AGG CCA TGG GCA GTG GCC AGG CGG GTG CTG    267

50  Thr Ala Ile Leu Ile Leu Gly Leu Leu Leu Cys Phe Ser Val Leu     64
268  ACA GCT ATC CTG ATT TTG GGC CTG CTC CTT TGT TTT TCT GTG CTT    312

65  Leu Phe Tyr Asn Phe Gln Asn Cys Gly Pro A
313  TTG TTC TAC AAC TTC CAG AAC TGT GGC CCT C gtaagcaagatcccagaccccccaa....0.26kb
```

FIG-2D

EXON 4 (SEQ ID NO:40)
344-520

```
                            cccagctctgagctttcccccacagGC CCC TGT GAG ACA        79
                                                     rg Pro Cys Glu Thr      357

80  Ser Val Cys Leu Asp Leu Arg Asp His Tyr Leu Ala Ser Gly Asn               94
358  TCT GTG TGT TTG GAT CTC CGG GAT CAT TAC CTG GCC TCT GGG AAC              402

95  Thr Ser Val Ala Pro Cys Thr Asp Phe Phe Ser Phe Ala Cys Gly              109
403  ACA AGT GTG GCC CCC TGC ACC GAC TTC TTC AGC TTT GCC TGT GGA              447

110  Arg Ala Lys Glu Thr Asn Asn Ser Phe Gln Glu Leu Ala Thr Lys              124
448  AGG GCC AAA GAG ACC AAT AAT TCT TTT CAG GAG CTT GCC ACA AAG              492

125  Asn Lys Asn Arg Leu Arg Arg Ile Leu G
493  AAC AAA AAC CGA CTT CGG AGA ATA CTG G gtgaggaaagcaggggtggaagatgc.... "2.6kb
```

FIG-2E

EXON 5 (SEQ ID NO:41)
521-645

```
                                                             lu Val Gln Asn Ser Trp        139
          tttagtccctcactcccatgcttcctttcctag AG GTC CAG AAT TCC TGG        537

140  His Pro Gly Ser Gly Glu Glu Lys Ala Phe Gln Phe Tyr Asn Ser           154
538  CAC CCA GGC TCT GGG GAG GAG AAA GCC TTC CAG TTC TAC AAC TCC           582

155  Cys Met Asp Thr Leu Ala Ile Glu Ala Ala Gly Thr Gly Pro Leu           169
583  TGC ATG GAT ACA CTT GCC ATT GAA GCT GCA GGG ACT GGT CCC CTC           627

170  Arg Gln Val Ile Glu Glu
628  AGA CAA GTT ATT GAG GAG gtgagaaaagttgggatattaactt......0.33kb
```

FIG-2F

EXON 6  (SEQ ID NO:42)
646-792

```
              tcagcccctctctcctttaaag Leu Gly Gly Trp Arg Ile Ser Gly Lys    184
                                     CTT GGA GGC TGG CGC ATC TCT GGT AAA    672

185           Trp Thr Ser Leu Asn Phe Asn Arg Thr Leu Arg Leu Leu Met Ser    199
673           TGG ACT TCC TTA AAC TTT AAC CGA ACG CTG AGA CTT CTG ATG AGT    717

200           Gln Tyr Gly His Phe Pro Phe Arg Ala Tyr Leu Gly Pro His        214
718           CAG TAT GGC CAT TTC CCT TTC AGA GCC TAC CTA GGA CCT CAT        762

215           Pro Ala Ser Pro His Thr Pro Val Ile Gln                       
763           CCT GCC TCT CCA CAC ACA CCA GTC ATC CAG gtgagggatgcactggcgaagacac...."3.2kb
```

FIG-2G

EXON 7 (SEQ ID NO:43)
793-855

```
                                                      Ile Asp Gln Pro Glu    229
          tctctccagtctctcttgtgccag                     ATA GAC CAG CCA GAG    807

230  Phe Asp Val Pro Leu Lys Gln Asp Gln Glu Gln Lys Ile Tyr Ala              244
808  TTT GAT GTT CCC CTC AAG CAA GAT CAA GAA CAG AAG ATC TAT GCC              852

245  Gln
853  CAG  gtaagatggcacatggacaaaggcc.....0.093kb
```

FIG-2H

EXON 8 (SEQ ID NO:44)
856-1044

```
                                                                                   tgtgactgacattccttcctc
           Ile Phe Arg Glu Tyr Leu Thr Tyr Leu Asn Gln Leu Gly Thr              259
       cag ATC TTT CGG GAA TAC CTG ACT TAC CTG AAT CAG CTG GGA ACC              897

260    Leu Leu Gly Gly Asp Pro Ser Lys Val Gln Glu His Ser Ser Leu              274
898    TTG CTG GGA GGA GAC CCA AGC AAG GTG CAA GAA CAC TCT TCC TTG              942

275    Ser Ile Ser Ile Thr Ser Arg Leu Phe Gln Phe Leu Arg Pro Leu              289
943    TCA ATC TCC ATC ACT TCA CGG CTG TTC CAG TTT CTG AGG CCC CTG              987

290    Glu Gln Arg Arg Ala Gln Gly Lys Leu Phe Gln Met Val Thr Ile              304
988    GAG CAG CGG CGG GCA CAG GGC AAG CTC TTC CAG ATG GTC ACT ATC              1032

305    Asp Gln Leu Lys
1033   GAC CAG CTC AAG gtgcctggaactggggggcagaaga.....0.23k
```

FIG-2

EXON 9
1045-1193 (SEQ ID NO:45)

```
                                  Glu Met Ala Pro Ala Ile Asp Trp Leu Ser Cys    319
    gtgtccctcctctaag GAA ATG GCC CCC GCC ATC GAC TGG TTG TCC TGC                  1077
320 Leu Gln Ala Thr Phe Thr Pro Met Ser Leu Ser Pro Ser Gln Ser                  334
1078 TTG CAA GCG ACA TTC ACA CCG ATG TCC CTG TCC CCT TCT CAG TCC                  1122
335 Leu Val Val His Asp Val Glu Tyr Leu Lys Asn Met Ser Gln Leu                  349
1123 CTC GTG GTC CAT GAC GTG GAA TAT TTG AAA AAC ATG TCA CAA CTG                  1167
350 Val Glu Glu Met Leu Leu Lys Gln Ar
1168 GTG GAG GAG ATG CTG CTA AAG CAG AG gttcgccgcaggtgggattggggag.....″1.3kb
                                                                          ctcagcttt
```

FIG-2J

EXON 10 (SEQ ID NO:46)
1194-1323

```
                gtgtgggtctctttgtctcccatag G Asp Phe Leu Gln Ser His   364
                                         G GAC TTT CTG CAG AGC CAC  1212

365  Met Ile Leu Gly Leu Val Val Thr Leu Ser Pro Ala Leu Asp Ser     379
1213 ATG ATC TTA GGG CTG GTG GTG ACC CTT TCT CCA GCC CTG GAC AGT    1257

380  Gln Phe Gln Glu Ala Arg Arg Lys Leu Ser Gln Lys Leu Arg Glu     394
1258 CAA TTC CAG GAG GCA CGC AGA AAG CTC AGC CAG AAA CTG CGG GAA    1302

395  Leu Thr Glu Gln Pro Pro Met
1303 CTG ACA GAG CAA CCA CCC ATG gtgaggaggaggagcgggtgtattg...."6kb
```

FIG-2K

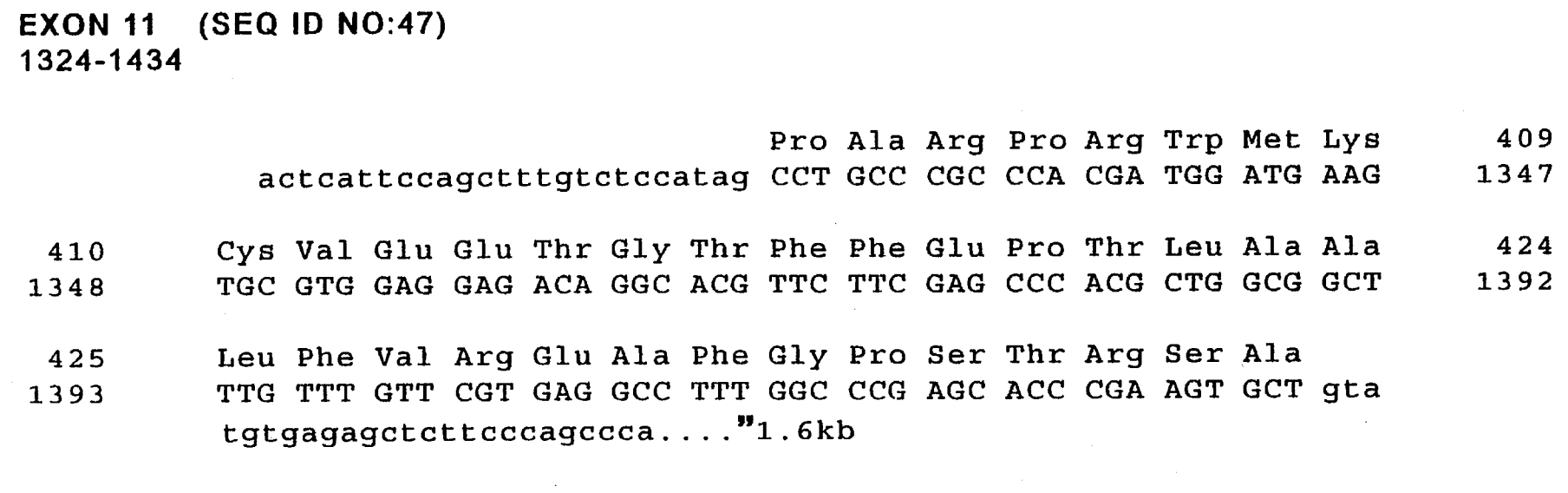

EXON 11 (SEQ ID NO:47)
1324-1434

```
                                Pro Ala Arg Pro Arg Trp Met Lys      409
           actcattccagcttgtctccatag CCT GCC CGC CCA CGA TGG ATG AAG   1347
410  Cys Val Glu Glu Thr Gly Thr Phe Phe Glu Pro Thr Leu Ala Ala     424
1348 TGC GTG GAG GAG ACA GGC ACG TTC TTC GAG CCC ACG CTG GCG GCT     1392
425  Leu Phe Val Arg Glu Ala Phe Gly Pro Ser Thr Arg Ser Ala
1393 TTG TTT GTT CGT GAG GCC TTT GGC CCG AGC ACC CGA AGT GCT gta
     tgtgagctcttcccagccca...."1.6kb
```

FIG-2L

EXON 12 (SEQ ID NO:48)
1435-1533

```
                                                         Ala      439
                         ctgtccctgactcactcccacag GCC              1437

Met Lys Leu Phe Thr Ala Ile Arg Asp Ala Leu Ile Thr Arg Leu  454
440  ATG AAA TTA TTC ACT GCG ATC CGG GAT GCC CTC ATC ACT CGC CTC  1482
1438

Arg Asn Leu Pro Trp Met Asn Glu Thr Gln Asn Met Ala Gln      469
455  AGA AAC CTT CCC TGG ATG AAT GAG ACC CAG AAC ATG GCC CAG      1527
1483

Asp Lys
470  GAC AAG gtcaggccaggcgtcctggctggtg....0.24kb
1528
```

FIG-2M

EXON 13 (SEQ ID NO:49)
1534-1611

```
                                                                          tagcctctt
                           Val Ala Gln Leu Gln Val Glu Met Gly Ala Ser      482
     ctgtgtctctcccag GTT GCT CAA CTG CAG GTG GAG ATG GGG GCT TCA           1566

Glu Trp Ala Leu Lys Pro Glu Leu Ala Arg Gln Glu Tyr Asn Asp           497
 483  GAA TGG GCC CTG AAG CCA GAG CTG GCC CGA CAA GAA TAC AAC GAT          1611
1567
      gtgggtccctgtgtttccagctcc....0.44kb
```

FIG-2N

EXON 14 (SEQ ID NO:50)
1612-1712

```
                                                     499        Ile Gln
                                                    1617 aagtcacctcctgcctcttccccag ATA CAG
500  Leu Gly Ser Ser Phe Leu Gln Ser Val Leu Ser Cys Val Arg Ser
1618 CTT GGA TCG AGC TTC CTG CAG TCT GTC CTG AGC TGT GTC CGG TCC
515  Leu Arg Ala Arg Ile Val Gln Ser Phe Leu Gln Pro His Pro Gln
1663 CTC CGA GCT AGA ATT GTC CAG AGC TTC TTG CAG CCT CAC CCC CAA
530  His Ar
1708 CAC AG gtatgacagcagggggagacacaggc.....0.19kb
```

FIG-20

EXON 15  (SEQ ID NO:51)
1713-1823

```
                                                               gagttcacatgtcctcttcc              544
         g Trp Lys Val Ser Pro Trp Asp Val Asn Ala Tyr Tyr Ser                                   1752
cacag    G TGG AAG GTG TCC CCT TGG GAC GTC AAT GCT TAC TAT TCG 545    Val Ser Asp His Val Val Phe Pro Ala Gly Leu Leu Gln Pro                                   559
1753   GTA TCT GAC CAT GTG GTA GTC TTT CCA GCT GGA CTC CTC CAA CCC                                1797

560    Pro Phe Phe His Pro Gly Tyr Pro Ar
1798   CCA TTC TTC CAC CCT GGC TAT CCC AG gtatgggtcactctgtaagggtagg....0.15kb
```

FIG-2P

EXON 16  (SEQ ID NO:52)
1824-1891

```
                                                    g Ala Val Asn Phe Gly Ala    574
         gtcaaataagcccttgtctccctag A GCC GTG AAC TTT GGC GCT        1842

575    Ala Gly Ser Ile Met Ala His Glu Leu Leu His Ile Phe Tyr Gln
1843   GCT GGC AGC ATC ATG GCC CAC GAG CTG TTG CAC ATC TTC TAC CAG   1887

590    Leu L                                                         589
1888   CTC T gtgggtaacaggggggccactgggagg.....0.23kb                   1887
```

FIG-2Q

EXON 17
1892-2061 (SEQ ID NO:53)

```
                                        tgttctcttgtcccatttca
         eu Leu Pro Gly Gly Cys Leu Ala Cys Asp Asn His Ala Leu    604
    acag TA CTG CCT GGG GGC TGC CTC GCC TGT GAC AAC CAT GCC CTC   1932

605      Gln Glu Ala His Leu Cys Leu Lys Arg His Tyr Ala Ala Phe Pro    619
1933     CAG GAA GCT CAC CTG TGC CTG AAG CGC CAT TAT GCT GCC TTT CCA   1977

620      Leu Pro Ser Arg Thr Ser Phe Asn Asp Ser Leu Thr Phe Leu Glu    634
1978     TTA CCT AGC AGA ACC TCC TTC AAT GAC TCC CTC ACA TTC TTA GAG   2022

635      Asn Ala Ala Asp Val Gly Gly Leu Ala Ile Ala Leu Gln
2023     AAT GCT GCA GAC GTT GGG GGG CTA GCC ATC GCG CTG CAG gtatgca agtgtcaagggccacacagt....0.35kb
```

FIG-2R

EXON 18 (SEQ ID NO:54)
2062-2157

```
                                                       cccttctctacccaccccctacccag
                                                                                  Ala Tyr
                                                                                  GCA TAC    649
                                                                                             2067

650  Ser Lys Arg Leu Leu Arg His His Gly Glu Thr Val Leu Pro Ser
2068 AGC AAG AGG CTG TTA CGG CAC CAT GGG GAG ACT GTC CTG CCC AGC               664
                                                                                2112

665  Leu Asp Leu Ser Pro Gln Ile Phe Phe Arg Ser Tyr Ala Gln
2113 CTG GAC CTC AGC CCC CAG ATC TTC TTT CGA AGC TAT GCC CAG                   679
                                                                                2155 gtaggcagcggccacctcccgccac....."1.3kb
```

FIG-2S

EXON 19 (SEQ ID NO:55)
2158-2445

```
2158  ttcaataacctctcttcctgctcag                                                        2202

Val Met Cys Arg Lys Pro Ser Pro Gln Asp Ser His Asp Thr His    694
2203      GTG ATG TGT AGG AAG CCC AGC CCC CAG GAC TCT CAC GAC ACT CAC    2247

Ser Pro Pro His Leu Arg Val His Gly Pro Leu Ser Ser Thr Pro    709
2248      AGC CCT CCA CAC CTC CGA GTC CAC GGG CCC CTC AGC ACC CCA        2292

Ala Phe Ala Arg Tyr Phe Arg Cys Ala Arg Gly Ala Leu Leu Asn    724
2293      GCC TTT GCC AGG TAT TTC CGC TGT GCA CGT GGT GCT CTC TTG AAC

Pro Ser Ser Arg Cys Gln Leu Trp ***
2344      CCC TCC AGC CGC TGC CAG CTC TGG TAACTTGGTTACCAAAGATGCCACAGC    2343

2403      ACAGAAATATCGACCAACACCTCCCTGGTCACATCCATGGAATCAGAGCAAGATTTCCT    2402

TTCTGCTTCTGTTCCAAAAATAAAAGCTGGCACTTGGCTTCCG
```

FIG-3

(SEQ ID NO:56)

```
        -176
-185  gtcacagtgaagacaaaaggaggagaccaagggcaagattgcttggggagtgaagactc
                                          GATA-1
-125  cctccctcttctccccctgagaagctgagataaaggggaggagaagcctgggtgccccc
                                  CACCC box
-65   actgataagcaggctccacccgaggccagtcctgtgtctgggacaaggcgaaagag
      GATA-1                                              Sp1
           -1
-5    cagca GAA GTG CCC CTT CTC CAG GAT CAA GGA ACT GGG GCG GGG GGT
+43   GTT TCC TGG ACC CCA GTC CTC CGA ATC AGC TCC TAG AGT GGA ACC AGG
                                                          Met
+81   AAG GAT TCT GGA GCC ACA GAA GAT AGA CAG ATG gtaagtcccctttggagt
                                  GATA-1
```

K2 (SEQ ID NO:57)
185
Trp Thr Ser Leu Asn Phe Asn Arg Thr Leu Arg Leu Leu Met Ser
TGG ACT TCC TTA AAC TTT AAC CGA ACG CTG AGA CTT CTG ATG AGT

199

K1 (SEQ ID NO:58)
TGG ACT TCC TTA AAC TTT AAC CGA ATG CTG AGA CTT CTG ATG AGT
Trp Thr Ser Leu Asn Phe Asn Arg Met Leu Arg Leu Leu Met Ser

DIAGNOSTIC METHOD AND KIT FOR DETERMINING KELL BLOOD GROUP GENOTYPE

This invention was made with Government support under Grant HL35841 awarded by the NIH. The Government has certain rights in this invention.

FIELD OF THE INVENTION

This invention relates to a method for determining Kell blood group genotype. More particularly, the invention relates to a molecular genetic method for the determination of K1/K2 genotype.

BACKGROUND OF THE INVENTION

The Kell blood group system is a well-known but complex group of blood antigens, comprising over 20 different related antigens. Of these, the antigen K1 (K, Kell) is known to be the strongest immunogen among the 23 known phenotypes. Serologically, the K1 sublocus has an allelic relationship with a high frequency antigen K2 (k, Cellano). Approximately 9% of the population has the K1 red cell phenotype, and antibodies to K1 are developed in about 5% of persons receiving a single unit of incompatible blood (Ref. 1).

Hemolytic disease of the newborn (HDN) is usually associated with maternal alloimmunization to Rh(D), but K1 incompatibilities can also cause severe hemolytic disease in newborns (Refs. 2–7). K1 sensitization from a previous pregnancy can result in HDN and complications during subsequent pregnancies if the fetus is a K1 carrier. Similar types of problems can arise in the more rare case of K2 sensitization. The identification of the fetal K1/K2 genotype would be of particular significance in situations in which the father is a K1/K2 heterozygote. Since the mother must be a homozygote in order to have been previously sensitized, there is a 50% chance that the fetus with a K:1,2 father is in danger of HDN. Because of this 50% risk, identification of the homozygosity or heterozygosity of the K1/K2 genotype of the fetus in these pregnancies becomes important in order to aid in their proper management.

Kell antigens appear to be encoded in 5 sets of antithetical paired alleles expressing high and low prevalence antigens. Thus, K1 (K) and K2 (k) are products of alleles, as are K3 ($Kp^a$), K4 ($Kp^b$) and K21 ($Kp^c$); K6 ($Js^a$) and K7 ($Js^b$); K17 and K11; and K24 and K14. However, a number of high prevalence antigens such as K12, K13, K18 and K22 are independently expressed. These relationships, and their place in the Kell system, have been established through the years by serological analyses of informative families (Refs. 8–12). A recently developed immunological test, MAIEA, which uses monoclonal antibodies to different Kell antigens, indicates that certain of the identified antigens occur in spatially distinct regions of the glycoprotein (Ref. 13). Thus, K1/K2, and K6/K7 are close together, while K3/K4 epitope is in a different location and K18 is in yet another protein domain (Ref. 38). Kell inheritance is autosomal and codominant, and the gene for the Kell protein (KEL) has been mapped to chromosome 7q33 (Refs. 14–17).

A variety of studies, including a molecular cloning, established that Kell blood group antigens are carried on a 93 kDa type II glycoprotein (Refs. 18–24) found on the surface of red blood cells (Ref. 13). The Kell protein has a short, 46 amino acid, N-terminal domain in the cytoplasm, and a large C-terminal portion, of 665 amino acids, on the external surface of the red cell. All of the carbohydrates are N-linked (Ref. 25), probably located in 5 sites, at asparagines 93, 115, 191, 345 and 627. Early biochemical studies suggested that Kell antigens reside on a protein whose conformation is largely dependent on disulfide bonds (Ref. 26). The Kell protein has 16 cysteine residues, one in the transmembrane region and 15 in the external portion (Ref. 24). Reduction of red cells by sulfhydryl reagents results in loss of Kell antigens and exposure of some neo-epitopes (Ref. 26).

The determination of Kell genotype has heretofore been confined to methods of detecting and identifying Kell antigens. Such methods employ antibodies or other compounds which identify and interact with the Kell protein or portions thereof. For example, various antibodies specific for particular Kell antigens have been identified (Refs. 13, 22). Agglutination methods for detecting Kell protein and other blood group antigens are described in U.S. Pat. Nos. 5,324,479, 5,302,512, 5,213,963, 4,560,647, 4,403,042, 4,358,436, and 4,148,607. These methods provide information about expressed protein profiles, not about protein molecular structure or the molecular genetic makeup of the individual. Such methods provide limited information, and generally require blood samples from subjects being examined. Determining fetal Kell phenotype also normally requires a fetal blood sample. This involves a potentially dangerous procedure in which the fetus is susceptible to hemorrhage and possibly death. None of the methods previously described discloses any method by which Kell genotype might be determined.

As a result, there exists a need for a method of safely and conveniently detecting Kell genotype. It would also be desirable to provide a method for determining Kell genotype in a fetus without the requirement for obtaining blood samples. A test based on DNA samples taken from amniotic cells would allow the clinician to avoid the risk of harm to the fetus and to more accurately predict the potential of anti-K-associated HDN.

SUMMARY OF THE INVENTION

The present invention provides a diagnostic method for the differential determination of K1/K2 Kell blood group genotype in a patient. Preferably, the method is directed to detecting the Kell polymorphism locus determining K1/K2 genotype, which has now unexpectedly been found to reside in exon 6 of the Kell gene.

In one embodiment, the invention provides a diagnostic method for differential determination of K1/K2 genotype by detection of target nucleic acid sequences specific to K1 and/or K2. In this embodiment, the method includes:

amplifying a DNA sample obtained from a patient using a primer which amplifies only K1/K2 DNA including the locus which determines K1/K2 polymorphism to identify the presence of amplified DNA corresponding to K1 DNA or K2 DNA or both.

Preferably, when the primer employed in the method of the invention amplifies K1/K2 DNA without producing measurably different products for each of K1 DNA and K2 DNA, the method then further includes a step of exposing the DNA to a restriction enzyme which differentially cleaves K1 DNA and/or K2 DNA. A preferred restriction enzyme is BsmI which cuts at a restriction site which, it has now unexpectedly been found, occurs in K1 DNA but not in K2 DNA. Thus BsmI cleaves K1 DNA while leaving K2 DNA intact. The exposing of the K1/K2 DNA to a restriction enzyme is generally performed following amplification of the DNA obtained from the patient, but may be performed preceding such amplification. When the primer or primer set differentially amplifies K1 DNA and K2 DNA, measurably different products are obtained without the requirement for treatment of the DNA with a restriction enzyme.

In a preferred embodiment, the diagnostic method includes:

(a) obtaining DNA from a tissue sample from a patient;

(b) amplifying the DNA by polymerase chain reaction using a primer or primer set which amplifies only K1/K2 DNA;

(c) exposing the amplified DNA to a restriction enzyme which differentially cleaves K1 DNA and K2 DNA to produce a pattern of DNA fragments; and (d) separating the DNA fragments according to molecular weight to form a pattern of DNA fragments, wherein the pattern of DNA fragments provides specific information characterizing the K1/K2 genotype of the patient.

In another preferred embodiment, the diagnostic method includes:

(a) obtaining DNA from a tissue sample from a patient;

(b) amplifying the DNA by polymerase chain reaction using a primer or primer set comprising at least one primer which amplifies only K1 DNA and at least one primer which amplifies only K2 DNA; and (c) separating the amplified DNA according to molecular weight to form a pattern DNA fragments, wherein the pattern of DNA fragments provides specific information characterizing the K1/K2 genotype of the patient.

In another preferred embodiment, the diagnostic method includes:

(a) obtaining DNA from a tissue sample from a patient;

(b) amplifying the DNA by ligase chain reaction using a primer set which amplifies only K1/K2 DNA to produce a pattern of DNA fragments; and (c) separating the DNA fragments according to molecular weight to form a pattern of DNA fragments, wherein the pattern of DNA fragments provides specific information characterizing the K1/K2 genotype of the patient.

In another embodiment, the diagnostic method includes:

(a) obtaining DNA from a tissue sample from a patient;

(b) exposing the DNA to a restriction enzyme which differentially cleaves K1 DNA and K2 DNA to produce a pattern of DNA fragments;

(c) amplifying the pattern of DNA fragments by polymerase chain reaction using a primer or primer set which amplifies only K1/K2 DNA; and (d) separating the amplified DNA according to molecular weight to form a pattern of DNA fragments, wherein the pattern of DNA fragments provides specific information characterizing the K1/K2 genotype of the patient.

In still another embodiment, the invention provides a diagnostic method which includes:

(a) obtaining DNA from a tissue sample from a patient;

(b) exposing the DNA to a restriction enzyme which differentially cleaves K1 DNA and K2 DNA to produce a pattern of DNA fragments;

(c) separating the DNA fragments according to molecular weight to form a pattern of DNA fragments; and (d) determining the presence of K1 DNA and/or K2 DNA using detectably labeled Kell cDNA probes;

wherein the pattern of DNA fragments provides specific information characterizing the K1/K2 genotype of the patient. Such methods include, for example, Southern blot methods such as are known in the art.

In an alternative embodiment, the invention provides a diagnostic method for detecting a target nucleic acid which is specific to K1 or K2. In this embodiment, the method includes:

(a) obtaining a nucleic acid fraction from a tissue sample from a patient;

(b) ascertaining the presence in the nucleic acid fraction of a target nucleic acid encoding at least a part of the Kell protein and including the site characterizing the K1/K2 polymorphism. In this method, the presence of the target nucleic acid is ascertained by means of a probe nucleic acid which includes a nucleic acid sequence which is known to specifically bind to or hybridize with K1 DNA or K2 DNA or transcripts thereof. The probe nucleic acids useful in this method may be any of the Kell-based oligomers described herein, including those which are detectably labeled or attached to a substrate. This method may be used to detect target nucleic acids which are chromosomal or genomic DNA, mRNA, and cDNA, as well as other related forms of nucleic acid encoding the K1/K2 domain of the Kell protein. Such methods include, for example, dot blot methods such as are known in the art.

In the diagnostic methods of the invention which require a primer or primer set, the primer or primer set may include a single primer, or may include a plurality of primers, including, for example, a plurality of primer pairs. For example, in a preferred mode, the method of the invention may employ a primer which specifically amplifies K1 DNA (K1 specific primer), a primer which specifically amplifies K2 DNA (K2 specific primer), and two primers which each amplify both K1 and K2 DNA (K1/K2 specific primers). In this mode, different sized PCR products are produced which correspond to a K1 DNA, K2 DNA and K1/K2 DNA. The pattern of PCR fragments serves to differentiate among K1/K1, K2/K2, and K1/K2 genotypes.

An especially preferred oligonucleotide primer specific for K1 comprises a nucleotide sequence selected from the group of nucleotide sequences including: ATA CTG ACT CAT CAG AAG TTT CAG CA (SEQ ID NO: 1), and ATA CTG ACT CAT CAG AAG TCT CAG CA (SEQ ID NO:2).

An especially preferred oligonucleotide primer specific for K2 comprises the nucleotide sequence: TGG ACT TCC TTA AAC TTT AAC TGA AC (SEQ ID NO:3).

An especially preferred K1/K2 specific oligonucleotide primer comprises a nucleotide sequence selected from the group of nucleotide sequences including: TTT AGT CCT CAC TCC CAT GCT TCC (SEQ ID NO: 4), and TAT CAC ACA GGT GTC CTC TCT TCC (SEQ ID NO: 5).

The molecular genetic method of the invention generally involves obtaining DNA from a biological sample from a human subject or patient. Typically, the method requires a blood sample, but other types of tissue samples which contain erythroid tissue are useful. In a particularly preferred embodiment, the invention provides a method for determining K1/K2 Kell blood group genotype in a fetus. In this embodiment, the preferred tissue sample includes a sample of amniotic fluid. It is also desirable in certain situations to employ the genotype determination method of the invention in conjunction with a standard Kell serological test to also determine Kell phenotype. It is understood that such samples can be obtained from sample libraries or tissue archives such as blood banks, or from forensic evidence, etc. Accordingly, the method may be used on a unique or irreplaceable sample or may be used to screen large numbers of samples.

In another embodiment, a diagnostic kit is provided for determining Kell blood group genotype in a sample of tissue from a patient. In this embodiment, the invention provides a diagnostic kit for determining Kell blood group genotype by detecting target nucleic acid sequences, such as sequences specific to K1 and K2. The kit includes amplification primers, i.e., oligonucleotides that bind to or cause elongation through sequences specific to K1 and K2. The in vitro kit further includes a container, such as a microtiter plate having a plurality of wells, having bound thereto oligonucleotide capture probes having nucleic acid sequences substantially complementary to the K1 and K2 target sequences.

In still another embodiment, the invention provides a method for the determination of Kell blood group genotype. In this embodiment, the method includes the steps of:

(a) selecting a probe nucleic acid sequence substantially corresponding to at least part of a known Kell exon or a transcript thereof, wherein the known Kell exon comprises a Kell polymorphism locus and codes for a specific Kell allele;

(b) contacting a sample nucleic acid sequence obtained or derived from a subject, the subject having an unknown phenotype with respect to the Kell polymorphism locus, with the probe nucleic acid sequence under conditions which permit hybridization when the nucleic acid sequences are significantly complementary; and (c) measuring an amount of hybridization between the probe nucleic acid sequence and the sample nucleic acid sequence.

In this embodiment, the detection of an amount of hybridization corresponding to an amount resulting from significantly complementary sequences indicates that the subject possesses the specific Kell allele under investigation. On the other hand, detection of an abnormally low amount of hybridization indicates that the subject lacks the specific Kell allele being investigated.

The invention further provides Kell-based nucleic acid oligomers which are at least substantially complementary to portions of the Kell gene, including, for example, the locus characterizing the K1/K2 blood type polymorphism. In particular, the invention provides nucleic acid oligomers which include a nucleic acid sequence substantially complementary to K1 DNA, as well as oligomers which include a nucleic acid sequence substantially complementary to K2 DNA. Moreover, the invention provides nucleic acid oligomers which include a nucleic acid sequence substantially homologous to K1 DNA, as well as oligomers which include a nucleic acid sequence substantially homologous to K2 DNA. The oligomers of the invention preferably include a nucleic acid sequence which is at least in part, exactly complementary or exactly homologous to a target region of the K1/K2 locus. Exact complementarity or homology ensures virtually unique recognition of, or hybridization with, a target nucleic acid.

The nucleic acid oligomers of the invention may be used as probes or primers to identify the presence of target nucleic acid sequences, such as K1/K2 sequences, through binding to or hybridizing with such target sequences. Accordingly, the nucleic acid oligomers may be detectably labeled by being linked to a detectable marker moiety such as a fluorescent label, an electron dense substance, a reporter moiety, a specific or nonspecific binding moiety, or other detectable moiety such as is known in the art. Optionally, the oligomers of the invention may further include a reactive moiety permitting cross-linking with a target nucleic acid sequence. Furthermore, the oligomers of the invention may be linked to a substrate, for example, to a gel or resin to immobilize the oligomers.

Moreover, the identification of the locus characterizing the K1/K2 polymorphism now permits the preparation of Kell-based polypeptides which include amino acid sequences which are substantially homologous to the K1 domain or to the K2 domain of the Kell protein. The polypeptides may be derived from natural sources and substantially purified or may be synthesized in substantially pure form as desired. Such polypeptides may also be detectably labeled, may be attached to reactive moieties, and may be bound to a substrate in accordance with methods known in the art. The polypeptides of the invention are useful as probes for, for example, detecting alloimmunization in a subject or patient. In such an assay, the polypeptide may comprise an amino acid sequence which is substantially homologous to K1 antigen and presents an immunologic profile which permits specific reaction with anti-K 1 antibodies.

Thus in another embodiment, the invention provides a diagnostic method for detecting alloimmunization of a patient to a Kell antigen, preferably K1 antigen. In this embodiment, the method includes obtaining a blood sample from a patient or subject, and measuring a parameter of immune reactivity of the sample with a polypeptide probe. The polypeptide probe preferably includes an amino acid sequence which is substantially homologous to the K1/K2 domain of the Kell protein. Moreover, it is desirable that the polypeptide probe be specifically reactive with anti-K1 antibodies present in the sample.

The invention further provides diagnostic kits for acquiring information about Kell genotype and Kell gene product expression in subjects. For example, the invention provides a diagnostic kit for the differential determination of K1/K2 genotype. In this embodiment, the in vitro kit includes:

(a) a primer or probe specific for a region of Kell DNA including the locus which determines a Kell polymorphism; and (b) a container. Preferably, the primer or probe is specific for a region of K1/K2 DNA, including the locus which determines the K1/K2 polymorphism.

Alternatively, the invention provides a diagnostic kit for determining Kell blood group genotype by detecting target nucleic acid sequences specific to particular Kell antigens, such as K1 and K2. In this embodiment, the kit includes:

(a) a primer set including first and second PCR primers wherein the first PCR primer is an oligonucleotide that will bind to or cause elongation through a sequence specific to K1 and the second PCR primer is an oligonucleotide that will bind to or cause elongation through a sequence specific to K2; and (b) a container, such as a microtiter plate having a plurality of wells, having bound thereto oligonucleotide capture probes having a nucleic acid sequence substantially complementary to the target sequences.

The invention further provides expression recombinant vectors which carry Kell nucleic acid sequences. Such vectors permit transformation of cells, particularly eukaryotic cells such as yeast and human cells, to cause such cells to express a heterologous protein product. The invention provides expression vectors which include a nucleic acid sequence which encodes at least a part of the Kell protein including a part of the protein which encodes a site of Kell polymorphism. In particular, the invention provides expression vectors which carry K1 cDNA permitting transformation of cells to produce transformed cells or transformants which express K1 protein on their cell surfaces. The invention also provides a stable cell line which has been modified (i.e., transformed) to express protein on its cell surface, as well as a method for transforming a cell line to express such protein. Preferably such protein includes at least the K1 domain, and more preferably, the protein is K1 protein. Methods for preparing expression recombinant vectors, and for transforming cell lines using such vectors are known in the art, and are described generally in Glick et al. Chapter 5 (Ref. 60), the disclosure of which is expressly incorporated herein by reference.

Accordingly, as a result of the invention, there is now provided a safe and convenient diagnostic method for differentially determining the Kell genotype of patients. In particular, there is now provided a method for determining Kell genotype in a fetus in utero without requiring the taking of a blood sample. A test based on determining Kell genotype, in particular K1/K2 genotype, from DNA obtained from amniotic fluid now allows the clinician to reduce the degree of risk to the fetus being tested. Moreover, the new diagnostic method permits the accurate prediction of the potential of anti-K-associated hemolytic disease of the newborn.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawing, wherein:

FIG. 2A–2S shows the nucleotide sequences of the exons of the Kell gene.

FIG. 3 shows the 5' flanking region and exon 1 of the Kell gene.

DETAILED DESCRIPTION OF THE INVENTION

Figure 1:
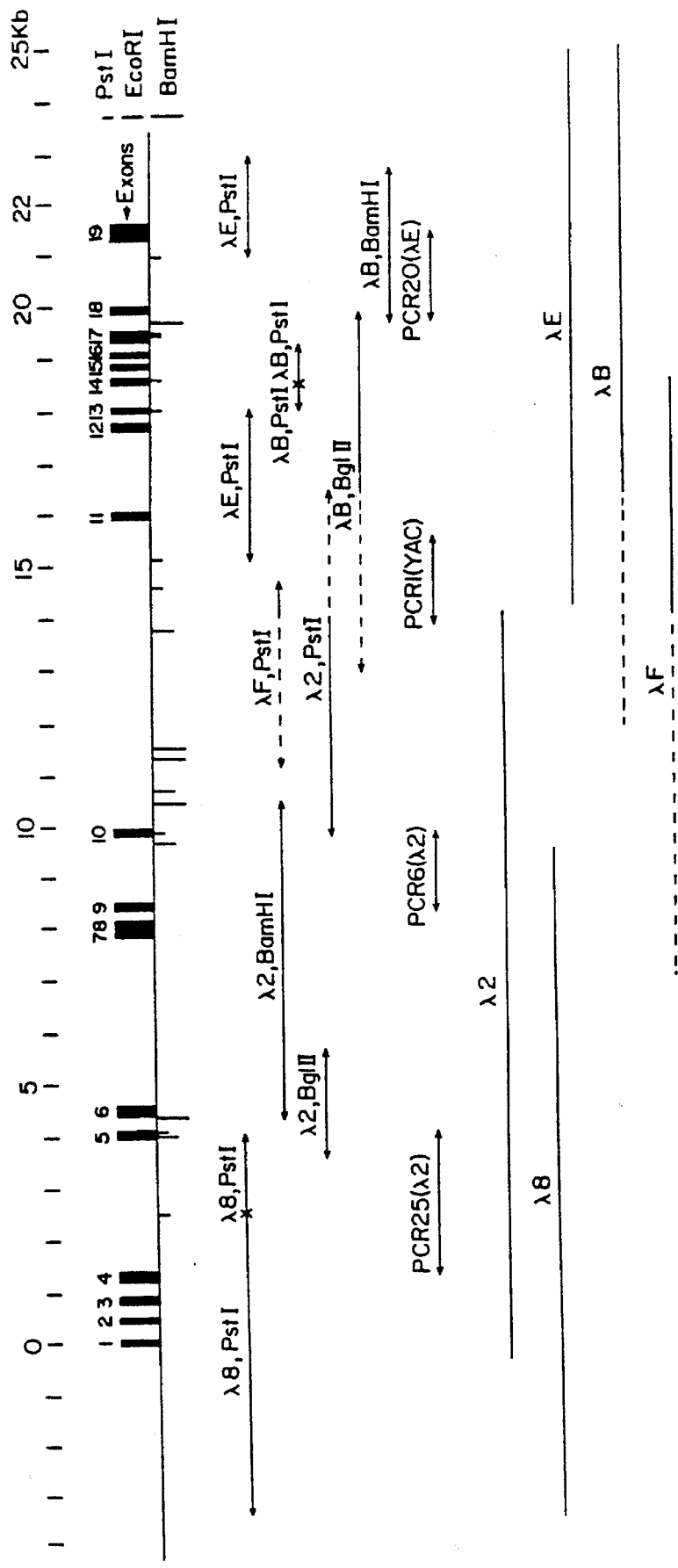
FIG. 1 shows a map of the Kell gene indicating the loci of the Kell exons, the relationships among the clones used to establish the exon locations, as well as restriction sites in the Kell gene.

The Kell blood group system is distinguished by its antigenic complexity (Ref. 12). Over 20 different antigens have been ascribed to the Kell system. A majority of the antigens are organized in 5 antithetical sets of high and low frequency antigens, with other Kell antigens being independently expressed. The molecular basis for this antigenic diversity has not previously been understood. The present invention, which involves description of the organization of the KEL gene and the boundaries of its 19 exons, now enables the molecular characterization of the different Kell phenotypes.

The molecular basis of the different Kell phenotypes has not previously been determined. Having now studied the structure of the KEL gene, and identified for the first time the 19 exons which encode Kell protein, the molecular basis of the K1/K2 polymorphism has now been determined by sequencing the exons of K1/K1 DNA and comparing them to K2/K2 sequences. It has now unexpectedly been found that base substitution in exon 6 of the K1 genotype predicts an amino acid change. This base substitution also creates a restriction enzyme site which has been employed to test over 40 different samples to confirm that the base substitution identifies the K1 genotype.

"Polymorphic" or "DNA polymorphism" refers to the condition in which two or more variations of a specific DNA sequence coexist in the same interbreeding population. Polymorphic differences are caused by differences in amino acid sequence which may be due to point mutations, gene rearrangements or alternative splicing.

"Restriction fragment length polymorphism" or "RFLP" refers to the differences in DNA nucleotide sequences that are randomly distributed throughout the entire genome and that produce different restriction endonuclease patterns for different individuals upon digestion of genomic DNA.

The most prevalent Kell phenotype is K:–1, 2, –3, 4, –6, 7, 9, 11, 12, 14, 18, 19, 22. We have now defined the 19 exons of the Kell gene (KEL) of a person with common Kell phenotype. To determine the molecular basis of K1/K2 polymorphism we designed a series of primers which would amplify the 19 exons of KEL and compared the DNA sequences of K1/K1 and K2/K2 DNA. The only base change which would encode a different amino acid was found in exon 6, and changed a threonine to a methionine at a consensus N-glycosylation motif (Asn.X.Thr→Met). This change would prevent N-linked glycosylation at this site. Based on the amino acid sequence of Kell protein of common phenotype, there are 6 possible N-glycosylation sites, i.e., asparagine residues 93, 115, 191, 345, 627 and 724. However, the asparagine at position 724 is probably not glycosylated because it is part of a sequence Asn.Pro.Ser and the presence of proline between asparagine and serine/threonine inhibits N-glycosylation (Ref. 27). In any event, changing threonine to methionine at position 193 would prevent glycosylation at asparagine 191. Thus, K1 protein would be composed of at most 4 instead of 5 carbohydrate moieties. Lack of a carbohydrate side-chain may expose different parts of the protein leading to immunogenicity. The loss of glycosylation in a red cell surface protein can lead to a change in blood group phenotype. The Webb glycophorin C variant also lacks an N-glycan (Refs. 28–29).

It has also now been observed that the point mutation from C to T in exon 6 creates a new restriction enzyme site, 5'-GAATGCT-3', which can be cut by BsmI, a well known restriction endonuclease. The use of restriction enzyme digestion allows the differentiation of K1/K1 and K2/K2 homozygotes and of K1/K2 heterozygotes, permitting the development of a diagnostic genotype procedure.

While not wishing to be bound by theory, it is known that, in very rare cases, red blood cells will be observed which do not express any Kell antigens. In this phenotype, known as $K_o$ (null), the red cells appear not to have any Kell protein on the cell membrane. Yet, preliminary experiments in our laboratory indicate that two $K_o$ persons contain Kell mRNA in peripheral blood and that the sequence of the mRNA from the initiation ATG codon to the poly A tail is identical to mRNA obtained from persons with common Kell phenotype. This indicates that the base sequences in the 19 exons of K2 and of some $K_o$ persons are identical. Therefore, PCR amplification of exon 6 and genotyping by treatment with BsmI could indicate a K2 genotype in $K_o$ persons. Serological analysis easily detects the $K_o$ homozygote, but the $K_o$ heterozygotes would be serologically identified as K2 or K1, and BsmI analysis would provide no further discrimination. Presumably the same would occur in the Kmod phenotypes in which expression of all Kell-related antigens are weakened. Nonetheless, for practical purposes, such ambiguous phenotypes are less clinically significant since $K_o$ and Kmod phenotypes are very rare. $K_o$ heterozygotes would be phenotypically, and therefore clinically, equivalent to K1 or K2 homozygotes. What is generally important in K1-sensitized pregnancies is to identify whether the fetus is a K1 carrier or not. The method of the invention now allows identification of Kell genotype, including identification of the K1 gene.

The molecular genetic method described herein can easily be applied to DNA samples obtained from amniotic fetal cells and is useful in determining the K1/K2 genotype of the fetus. This test can assist in the identification of those pregnancies at risk for hemolytic disease of the newborn resulting from Kell alloimmunization.

For purposes of discussion herein, the gene encoding the Kell protein is designated the "Kell gene". The region of the Kell gene which encodes a specific domain of the Kell protein is termed a "Kell locus". For example, it has been determined as a result of the present invention that the K1 antigen and the K2 antigen are encoded by alleles of the Kell gene. More specifically, the K1 antigen and the K2 antigen are co-located in the same domain of the Kell protein, in which a single amino acid substitution has been found to result in the difference between Kell protein including the K1 antigen and Kell protein including the K2 antigen. This single amino acid substitution has now been found to arise from a single nucleotide substitution in the Kell gene. Thus, the portion of the Kell gene which includes this site of nucleotide variation is designated the "K1/K2 locus". When the K1/K2 locus encodes K1 antigen this region of the Kell gene is designated the "K1 locus". When the K1/K2 locus encodes K2 antigen, this region of the Kell gene is designated the "K2 locus". The K1/K2 locus is also said to be the site or locus which determines or characterizes the "K1/K2 polymorphism", i.e., the observed phenotypic difference between the K1 and K2 antigens.

For purposes of this invention, Kell protein which includes the K1 antigen or K1 domain is designated "K1 protein", while Kell protein which includes the K2 antigen or K2 domain is designated "K2 protein". Conversely, DNA encoding K1 protein may be termed "K1 DNA", while DNA encoding K2 protein may be termed "K2 DNA". A preferred K1 DNA according to the invention is K1 cDNA. It is also to be understood that other Kell-related or Kell-based chromosomal DNA (including exons and introns and parts thereof), nucleic acid templates, nucleic acid transcripts, as well as cDNA, may be similarly designated as K1/K2, K1, or K2, depending on context or application. Similar considerations apply in the context of other antigens in the Kell system.

As a result of the present invention, it is now possible to design probes and/or primers comprising nucleic acid oligomers or oligonucleotides which can be employed to detect polymorphisms in the Kell gene. The probes or primers suitable for this purpose preferentially hybridize with or are specific for a region of the Kell gene comprising a site or region in which a point change in nucleotide sequence causes a change in the Kell gene product characterizing the polymorphism. Accordingly, the probes or primers include those which hybridize with higher frequency alleles as well as those which hybridize with lower frequency alleles. In certain applications, it is desirable to define the presence of heterozygosity. In such cases probe or primer combinations enabling differential detection of two or more alleles and/or loci have been found to be useful.

For example, a probe of the invention may be said to bind to or hybridize with Kell DNA if it specifically recognizes a defined region of Kell DNA, such as a region which includes the K1/K2 polymorphism locus. A primer of the invention may be said to specifically amplify Kell DNA if it binds to or causes elongation through a defined region of Kell DNA. Thus, a primer specifically amplifies K1/K2 DNA if it preferentially amplifies a region including the K1/K2 locus. Accordingly, a K1/K2 primer amplifies DNA including the K1/K2 locus but non-selectively amplifies both K1 DNA and K2 DNA. On the other hand, a primer is specific for a particular allele, such as K1 (K1 primer), if it specifically amplifies only DNA associated with that allele, such as K1 DNA, while a primer specific for K2 (K2 primer) specifically amplifies only K2 DNA. Similar considerations apply to other alleles in the Kell system.

It is particularly preferred that probes be capable of differentiating two alleles which differ by no more than a single nucleotide modification. It is known in the art that it is possible to control the specificity of hybridization by selectively constructing probes and primers and by adjusting hybridization or other experimental conditions. There may be situations, however, in which it would be desirable to employ probes which hybridize somewhat less selectively. Accordingly, it is within a particular context that a probe or primer according to the invention is said to be "substantially complementary" to a specific Kell sequence. That is, if the situation demands high precision, a probe or primer is substantially complementary to a target sequence if there exists only a very small probability that the oligomer will bind with a sequence other than the specific target sequence. In other situations, a probe or primer may be deemed to be substantially complementary to a target sequence if the probability of a unique hybridization is substantially less than 1.0. Thus, a probe or primer of the invention may be "substantially complementary" to a target region if it is either exactly complementary, or even only partially complementary, to the target region, depending on the required stringency of the method parameters.

Thus, the invention provides probes and primers which hybridize with parts or all of the Kell locus. Such probes are useful when the Kell gene or transcripts thereof are desired to be characterized. Moreover, the invention provides probes and primers which include part or all of one or more introns in the Kell locus in chromosomal DNA. Such probes are useful when the Kell gene itself is desired to be characterized and additional information is desired to be obtained about the structure of the gene in a particular individual.

The probes or primers of the invention may also include, as part of their nucleotide sequences, regions which are not substantially complementary to any region adjacent to or near a target sequence. Thus, in any probe or primer of the invention, at least a part of the probe or primer is substantially complementary to a target segment.

"Amplification" refers to any molecular biology technique for detection of trace levels of a specific nucleic acid sequence by exponentially amplifying a template nucleic acid sequence. In particular, amplification techniques include such techniques as polymerase chain reaction (PCR) and ligase chain reaction (LCR). The PCR is known to be a highly sensitive technique, and is in wide use. The LCR is known to be highly specific, and is capable of detecting point mutations. In certain circumstances it is desirable to couple the two techniques to improve precision of detection. The PCR is a well-known technique and is described, for example, in Innis et al. (Ref. 30). The LCR is more recently developed and is described in Landegren et al. (Ref. 31) and Barany (Ref. 32). An LCR kit is available from Stratagene. Other amplification techniques may be expected to be employed according to the method of the invention.

"Primer" refers to an oligonucleotide, whether natural or synthetic, capable of initiating DNA synthesis for exponential amplification of a target or template nucleic acid sequence by an amplification technique. For PCR the primer acts as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. For LCR the primer is capable of annealing to a target nucleic acid and of being ligated to an adjacent primer to serve as a template for amplification. Also for purposes of the LCR, the primer generally includes paired sets of adjacent, complementary oligonucleotides which can anneal to single stranded target molecules and ligate them together. For LCR amplification of DNA, the primers include two sets of adjacent, complementary oligonucleotides.

A primer is preferably an oligodeoxyribonucleotide and is single stranded for maximum efficiency in amplification, but may also be double stranded. If double stranded, the primer is generally first treated to separate its strands before being used to prepare extension products. Typically. LCR primers are double stranded. The exact length of a primer will depend on many factors, but typically ranges from 15 to 25 nucleotides. Short primer molecules generally require cooler temperatures to form sufficiently stable hybrid complexes with the template. A primer need not reflect the exact sequence of the template but must be sufficiently complementary to hybridize with a template. An example of a non-complementary sequence which may be incorporated into the primer is a sequence which encodes a restriction enzyme recognition site (see U.S. Pat. No. 4,800,159).

"Primer," as used herein, may refer to more than one primer, particularly in the case where there is some ambiguity in the information regarding one or both ends of the target region to be amplified. For instance, if a nucleic acid sequence is inferred from a protein sequence, a "primer" is actually a collection of primer oligonucleotides containing sequences representing all possible codon variations based on the degeneracy of the genetic code. One of the primer oligonucleotides in this collection will be homologous with the end of the target sequence. Likewise, if a "conserved" region shows significant levels of polymorphism in a population, mixtures of primers can be prepared that will amplify adjacent sequences.

A primer or probe can be labeled, if desired, by incorporating a label detectable by spectroscopic, photochemical, biochemical, immunochemical, or chemical means. For example, useful labels include $^{32}$P, fluorescent dyes, electron-dense reagents, reporter molecules such as enzymes (as commonly used in ELISAs), biotin, or haptens or proteins for which antisera or monoclonal antibodies are available. A label can also be used to "capture" the primer, so as to facilitate the immobilization of either the primer or amplified DNA on a solid support.

"Oligonucleotide" or "nucleic acid oligomer" refers to primers, probes, nucleic acid fragments to be detected, nucleic acid controls, and unlabeling blocking oligomers and is defined as a molecule comprised of two or more deoxyribonucleotides or ribonucleotides. The nucleic acid oligomers of the invention may be single-stranded oligomers of deoxyribonucleic acid (DNA) or ribonucleic acid (RNA). The exact size of an oligonucleotide will depend upon many factors and the ultimate function or use of the oligonucleotide. The oligodeoxyribonucleotides and oligoribonucleotides may be obtained or derived by known methods from natural sources. Alternatively, the oligonucleotides may be produced synthetically according to methods known in the art. Such methods include, for example, cloning and restriction of appropriate sequences and direct chemical synthesis by a method such as the phosphotriester method of Narang et al. (Ref. 33); the phosphodiester method of Brown et al. (Ref. 34); the diethylphosphoramidite method of Beaucage et al. (Ref. 35); and the solid support method in U.S. Pat. No. 4,458,066. It is preferred that the oligomers be at least substantially purified to avoid introduction of artifacts into the genotype determination method.

The invention also provides oligonucleotides which are structurally homologous to a part or all of genetic material related to or derived from the Kell gene. An oligomer is said to be "substantially homologous" to another if, despite variations in the nucleotide sequence, the oligomer encodes an amino acid sequence which is phenotypically identical to the sequence to which it is being compared. Thus, sequences are not substantially homologous if, when expressed, the sequences result in shift in Kell phenotype. On the other hand, two sequences encoding the same locus or sublocus are substantially homologous if they are not identical but nonetheless encode sequences which correspond to parts or all of phenotypically non-differentiable variants of the Kell protein. Accordingly, sequences which encode K1 domain and sequences which encode the K2 domain are not substantially homologous, even though they differ, as has now been discovered, by a single nucleotide substitution. In contrast, variations in nucleotide sequence which do not result in an amino acid shift in the encoded gene product may be substantially homologous.

The Kell genotype determination methods of the invention are of particular utility in the determination of the genotype of fetuses to avoid hemolytic disease of the newborn. The methods of the invention are also useful in a variety of other situations in which molecular genetic information about a person is desired. For example, the methods of the invention are useful in situations in which it is desired to obtain information concerning the identity of an individual from forensic samples. Alternatively, the methods of the invention are useful for obtaining genetic information enabling the determination of paternity in those situations in which paternity is in doubt or dispute. In addition, the methods of the invention are useful for the determining the Kell genotype of a recipient of a blood transfusion, as well as for the screening of stored blood for Kell genotype, to avoid transfusion incompatibility. The peptide based methods of the invention are particularly useful in determining alloimmunization of a person to a Kell antigen, such as K1. Information about such alloimmunization would be expected to be useful in advising women about risk entailed in future pregnancies. Other applications of the methods of the invention will suggest themselves to the skilled artisan.

EXAMPLES

For each of the examples described herein, the molecular biology techniques employed were performed generally in accordance with methods accepted in the art. See, for example, Sambrook et al. (Ref. 36), and Innis et al. (Ref. 30), the disclosures of which are incorporated herein by reference.

Example 1

The organization of the KEL gene was determined using the following procedure.

Screening of a Genomic Library

A human placental genomic DNA library constructed in EMBL3 Sp6/T7 was obtained from Clontech, Inc. (Palo Alto, Calif.). The genomic DNA library was constructed by partially digesting human placenta genomic DNA with Sau3A1 and ligating the fragments into the BamHI site of the vector. For screening, the λ phage library was grown in either NM528 or LE392 strain of *E. coli* and plated. The DNA was lifted on Hybond™-N+ membranes (Amersham Co., Arlington Heights, Ill.) and hybridized with Kell cDNA probes according to standard procedures (Ref. 37). The cDNA probes were labeled with $^{32}P$ by random primer extension using a commercial kit (Boehringer Mannheim Inc., Indianapolis, Ind.). The specific activity of the probes was approximately $1\times10^8$ cpm/µg. Fourteen positive clones were isolated.

Characterization of Exons and Introns

Of the 14 positive clones identified, five (λ2, λ8, λB, λF, and λE) were selected for further characterization. Two of the clones (λ2 and λE) span most of the Kell gene and cover about 21.5 Kb (see FIG. 1). Clone λ8 was studied because it extended more of the 5' flanking region and also served to reconfirm the sequences determined from clone λ2. Clones λB and λF were used because they overlapped with λE, and in addition a small segment of λF overlapped with the 3' end of λ2 (see FIG. 1).

These five clones were initially mapped by digestion with XhoI plus PstI and with XhoI plus EcoRI, followed by Southern blot hybridization using different oligonucleotides specific for various locations in the Kell cDNA sequence. The genomic clones were then digested with the following enzymes: PstI, EcoRI, BamHI, BglII and XhoI, either individually or in combination. The individual gene fragments were subcloned into PUC18 (Gibco BRL, Gaithersburg, Md.) or pGEM-3Zf(+) (Promega Co.) and sequenced on an automated 373A DNA sequencer (Applied Biosystems, Inc., Foster City, Calif.). The exons, determined in relation to the Kell cDNA sequence, and their flanking regions, were fully sequenced, as were some short introns. With one exception, the long introns were sized by PCR using primers from the flanking regions of the introns. The longest intron, between exons 10 and 11, was partially sized using primers from known intron sequences obtained from λ2 and λE, using a YAC clone as template. (Seven yeast artificial chromosome (YAC) clones were separately isolated by PCR specific for KEL exon 6 from a YAC resource enriched for chromosome 7 DNA.) This area of the intron was confirmed by PCR using human genomic DNA as template.

Restriction Enzyme Mapping and Southern Blot Analysis of the Genomic Clones

Subclones were mapped with BamHI, EcoRI and PstI. The different sizes of digested DNA were resolved by agarose gel electrophoresis. The DNA fragments were in some cases further analyzed by Southern blots using $^{32}P$-labeled oligonucleotides derived from different locations of Kell cDNA and also identified with available sequences of the subcloned gene fragments. The combination of these procedures allowed a restriction map of BamHI, EcoRI and PstI to be constructed. Sequence analysis of the subcloned Kell gene fragments from these 5 genomic clones revealed that the human KEL gene contains 19 exons ranging in size from 63 bp (exon 7) to 288 bp (exon 19) which includes a 3' untranslated region.

FIG. 1 shows the newly determined structure of the human Kell gene (KEL) with restriction enzyme sites. The position of exons are shown as dark boxes and the introns are shown as lines connecting the exons. The vertical lines of different heights mark the restriction enzyme sites in the Kell gene. The λ phase, genomic clones are shown at the bottom of the diagram (λ2, λ8, λE, λB and λF). Two of the genomic clones from the commercial genomic library, clones λB and λF, gave inconsistent sequences when compared to other clones (λ2 and λ8). The 5' segments of clones λB and λF should be identical to the 3' segments of λ2 and λ8 but sequence analysis showed that they were different. The reason for this is not known, but could be due to ligation of DNA material during the preparation of the genomic library. These areas of difference are depicted in FIG. 1 by broken lines. The restriction enzyme digested products which were subcloned and analyzed are shown above the genomic clones. Each subclone shows the restriction enzymes used and the genomic clones from which it was derived. Four PCR-derived sub-clones (PCR25, PCR6, PCR1 and PCR20) are also shown. In parenthesis each PCR product shows the genomic clone from which it was amplified. A small segment of the large intron not covered by clones λ2, λ8 and λE was determined by sequencing PCR products (PCR6) from a YAC clone (yWSS679) and from the genomic DNA. This strategy was employed even though the λF clone covers the 3' end of the λ2 clone. This allowed us to cover the entire Kell gene and to size the intron between exons 10 and 11 without ambiguity.

All exon/intron splice junctions were found to contain the 5' donor −gt and the 3' acceptor −ag sequences. The introns ranged in size from 93 bp to approximately 6 kb. there were 6 introns which were longer than 1 kb (FIGS. 1 and 2). The long introns were not fully sequenced, but were sized by PCR. There was ambiguity in analyzing the intron between exons 10 and 11 because the 5' region of clones λB and λF, which were expected to overlap with the 3' region of clones λ2 and λ8, did not. These ambiguous areas of clones λB and λF are shown as dotted lines in FIG. 1. Because of this uncertainty, the small gap of the gene not covered by clones λ2 and λE was bridged by PCR amplification of YAC clone yWSS679 containing the Kell gene (FIG. 1). The size of this PCR amplified region was further confirmed by PCR of genomic DNA obtained from a person of common Kell phenotype using the same primers used for the YAC clone.

All of the exons were sequenced and compared to that of a full length Kell cDNA isolated from a human bone marrow library obtained from Clontech. The Kell phenotype of this library was unknown. Differences were noted in 4 bases in exon 3 as compared with the published sequence for Kell cDNA (Ref. 8). These differences were due to sequencing errors in the original study. The corrected sequences were submitted to EMBL/GenBank Updates (National Center for Biotechnology Information, Bethesda, Md.) under accession No. M64934. One no table difference is a base substitution in the membrane-spanning region, which encodes a leucine instead of proline. The corrected base sequences are shown in bold type in FIG. 2.

FIG. 2 illustrates the sequence of the individual exons encoding human Kell protein with the immediate intron flanking splice junction sequences. The base sequences of the individual exons are shown in capital letters and the flanking intron sequences in small letters. The amino acid sequences encoded by the exons are shown above the base sequences. The numbers on the left-side, below the indicated exons, refer to the base numbers from the cDNA. The other numbers on the left and right sides indicate the amino acid residues and the bases, as previously described for the cDNA (Ref. 24). Intron sizes are specified at the end of the exons. 5' and 3' splice sites are also shown.

Since the Kell phenotype of the person from whom the genomic DNA library was constructed is unknown, we isolated RNA from peripheral blood of a person of known common phenotype (K:−1,2,−3,4,−6,7). cDNA was prepared by RNA-PCR and sequenced according to methods known in the art. The deduced amino acid sequence was identical to that shown in FIG. 2 as obtained from the Clontech genomic library. In the person of known phenotype, C to T base differences occurred in two locations (nt 1656 and 1664), but these substitutions did not change the predicted amino acids.

Of interest is that exon 1 includes the 5' untranslated region and codes for only initiation methionine. The single membrane spanning region is located in exon 3 and the pentameric sequence (HELLH) (SEQ ID NO:59) which conforms with a consensus sequence (HEXXH) (SEQ ID NO:60) found in the active sites of zinc neutral endopeptidases (Ref. 38) is in exon 16 (FIG. 2).

The coding region of the native protein is present in 18 of the 19 exons; the first exon contains the 5' untranslated region and the initiation methionine. Other examples having only the initiation codon in the first exon are known (Ref. 39). The single transmembrane region is encoded in exon 3 with exons 4 to 19 encoding most of the extracellular portion. The HEXXH (SEQ ID NO:60) motif, which is unique to zinc metallopeptidases (Ref. 38) is encoded in a 68 bp exon (exon 16). In addition to the consensus pentameric sequence, Kell has sequence and structural homology with a family of membrane-associated zinc neutral endopeptidases (EC24.11) (Ref. 24) of which the enkephalinases and CALLA are examples (Refs. 40–41). The CALLA gene is larger than the Kell gene, about 80 kb, and is composed of 24 exons (Ref. 42). In CALLA the putative enzyme active site is encoded in exon 19 and a comparison of base sequences of exons 18 and 19 of CALLA with exons 15 and 16 of Kell shows 54.5% base identity.

Example 2

Transcription Initiation Site

The transcription initiation site of the KEL gene was determined by the rapid amplification of cDNA ends (5' RACE) employing a human fetal library (5' RACE Ready™ cDNA library, Clontech Laboratories, Palo Alto, Calif.). The source of poly (A)+ RNA was normal liver pooled from 2 female Caucasian fetuses, 22 and 26 weeks of gestation. The single stranded cDNA library was made by reverse transcription, using random hexamers as primers. An oligonucleotide anchor 3'-NH$_3$-GGA GAC TTC CAA GGT CTT AGC TAT CAC TTA AGC AC-p-5' (SEQ ID NO:6) was ligated to the cDNA. For the 5' RACE, 2 sets of nested PCR reactions were carried out, using primers from 2 different locations on Kell cDNA (nt 132 and nt 178). In the first PCR, 5' RACE Ready™ cDNA was used as template. The primers used for one set (PCR1) included the anchor primer provided by Clontech (5'-CTG GTT CGG CCC ACC TCT GAA GGT TCC AGA ATC GAT AG-3') (SEQ ID NO:7) and Kell anti-sense primer (5'-CTC GGC TCT TCC TCA CTT TGG TCC-3', nt 132) (SEQ ID NO:8). For the other set (PCR2), the primers included the Clontech anchor primer (SEQ ID NO:7) and Kell anti-sense primer (5'-CTC TTG GCT CCA GAG AGT TCC CAT-3', nt 178) (SEQ ID NO:9). For the second nested PCR the products of the first PCR reactions were used as template and the Clontech anchor primer (SEQ ID NO:7) was again used as sense primer for both parallel reactions. In PCR1 a Kell anti-sense primer (5'-CCC ACC TTC CAT CTG TCT ATC TTC-3', nt 109) (SEQ ID NO:10) was used. For PCR2, the Kell anti-sense, nt 132, (SEQ ID NO:8) was used.

PCR was performed in an automated thermocycler (Minicycler, MJ Research Inc. Watertown, Mass.) using an initial cycle of 94° C. for 3 minutes, 62° C. for 1 minute, and 72° C. for 30 seconds. In cycles 2 to 30 the conditions were 94° C. for 30 seconds, 62° C. for 30 seconds and 72° C. for 30 seconds. In the last cycle the polymerization step at 72° C. was extended to 10 minutes. The final concentrations of reagents were 50 mM KCl, 10 mM Tris-HCl (pH 9.0), 3 mM MgCl$_2$, 400 nM of each primer, 200 µM of each dNTP, 0.1% Triton-X100, and 2.5 units of taq polymerase, in a final volume of 50 µL. The "hot start" method using AMPLI-WAX™ wax beads from Perkin Elmer (Branchburg, N.J.) was employed. The PCR products were separated by electrophoresis in 0.8% low melting agarose gels, eluted and directly ligated to pT7-Blue(R) plasmid vector from Novagen (Madison, Wis.) and transformed in DH5αF' strain E. coli.

Each primer yielded 3 different size products. These products were subcloned and sequenced. The largest product from each PCR reaction had a 5' end at 120 bp upstream from the initiation codon. The 2 shorter PCR products ended at 81 and 30 bp upstream from the initiation codon.

FIG. 3 illustrates the nucleotide sequence of the KEL 5' flanking region showing exon 1 and possible cis regulatory elements. A 185 bp region upstream from the probable cap site is shown. The three possible transcription initiation sites are marked by ∇. Consensus sequences for GATA-1, Sp1 and a CACCC region are boxed. The region −176 to −1, which was copied by PCR and placed in a CAT-expression vector is shown. The initiation methionine is in bold letters.

Three possible transcription initiation sites were found using the 5' RACE procedure and poly (A)+ RNA from fetal liver. The first of these cap sites, located 120 bp upstream from the initiation ATG, is also the 5' end of a cDNA cloned from a human bone cDNA library (Ref. 24) the other 2 sites are 81 and 30 bp upstream from the initiation codon. All 3 sites were obtained using 2 different Kell cDNA anti-sense primers. Although all 3 locations are purine bases and could act as transcription initiation sites. It is also possible that those at 81 and 30 bp upstream from the ATG are artifactual due to incomplete reverse transcription. This is unlikely given that random hexamers were used to prepare the cDNA library. However, secondary RNA structures can also cause premature termination of reverse transcription.

Example 3

Analysis of 5' Flanking Region

The constitution of the 5' flanking region was obtained by DNA sequencing of sub-clone λ8, following digestion with PstI (see FIG. 1). The 5' flanking region was determined to span nucleotides −176 to −1.

FIG. 3 shows a 185 bp sequence upstream from the first possible initiation transcription site. Analysis of this region, and of exon 1, indicates that there are no TATA sequences but several other possible transcription factor binding sites were noted. At least 2 GATA-1 sites are present close to a CACCC box. Sp1 and GATA-1 sequences are present in exon 1. The 5' flanking region contains purine-rich regions. These areas of interest are also shown in FIG. 3.

The transcriptional activity of the 5' flanking region from −176 to −1 (FIG. 3) was determined by CAT assay in transfected K562 cells as compared to the promoter-less pCAT vector. In this procedure, a PCR product spanning nucleotides −176 to −1 relative to the first cap site was subcloned into pCAT basic vector obtained from Promega Co. Cells of the erythroleukemic cell line K562 were then transfected using the lipofectin method. Construction of the CAT-vector, transfection and chloramphenicol acetyltransferase (CAT) activity were assayed following the protocol provided by Promega Co. CAT enzymatic activity was measured using [$^{14}$C]-chloramphenicol (50–60 mCi/mmol, Amersham Co., Arlington Heights, Ill.). The reaction products were measured by liquid scintillation spectrometry and analyzing the reaction products by thin layer chromatography. As a negative control the pCAT basic vector without promoter was used. All cell extracts were normalized by protein analysis in order to compare values.

Figure 4:
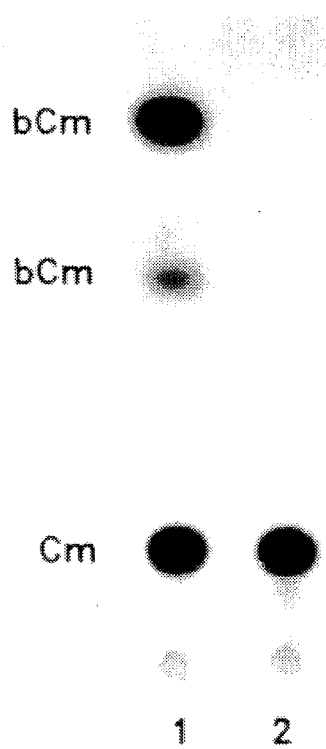
FIG. 4 shows an autoradiogram illustrating the promoter activity of the 5' flanking region of the Kell gene.

Introduced in front of a CAT reporter gene, the 5' flanking region exhibited promoter activity in the erythroleukemic cell line K562. pCAT vector with the 5' flanking region was found to express approximately 0.8 units of CAT activity per milligram of cell extract protein. A unit of CAT enzyme activity is defined as the amount of enzyme required to transfer 1 nmol of acetate of chloramphenicol in 1 minute at 37° C. FIG. 4 shows CAT activity of the 5' flanking region. An autoradiogram, exposed for 48 hours, is shown. Lane 1 has pCAT vector with the 5' flanking region and lane 2 has pCAT basic vector without promoter. The radioactive butyrylated chloramphenicol is indicated as "bCm", and the unreacted chloramphenicol is indicated as "Cm".

The putative promoter region does not contain the typical TATA box usually located −25 to 30 nt relative to the cap site (Ref. 43). However, as in several erythroid specific genes, consensus sequences for GATA-1 factor were found in the promoter region. In addition, possible Sp1 and GATA-1 binding sites were noted in exon 1. It is not known whether GATA-1 and Sp1 regulate KEL gene expression but GATA-1 is common in erythroid genes (Refs. 44–50) and is known to be expressed at low levels in hematopoietic progenitor cells and up-regulated during erythroid maturation (Refs. 51–53). If these transcription factors define erythroid tissue specificity it will be in agreement with our Northern blot studies which detected Kell transcripts in bone marrow and fetal liver but not in several non-erythroid tissues (Ref. 14).

Example 4

Analysis of the 3' End

Exon 19 is the largest Kell exon, encoding the C-terminal 53 amino acids and containing the 3' untranslated region with a polyadenylation signal 100 bp downstream of the termination codon. Previous Northern blot analysis showed that the major Kell transcript in bone marrow and fetal liver is 2.5 kb although smaller amounts of larger mRNAs, notably 6.6 kb, also were observed (Ref. 14). In originally cloning the Kell cDNA from a human bone marrow library, we isolated a cDNA with a large (3 kb) 3' untranslated region (Ref. 24).

To determine the 3' end structure of the Kell gene, RNA was isolated from peripheral blood as described by Goosens et al. (Ref. 54) and cDNA was prepared by reverse transcription and PCR amplification using a Perkin Elmer RNA PCR kit (Roche Molecular Systems, Inc., Branchburg, N.J.). First strand synthesis was initiated using an anchored oligo d(T)$_{16}$ primer. PCR amplification of the 3' end of Kell cDNA was performed using the anchor primer and an oligonucleotide primer from the coding sequence of Kell cDNA. The anchor antisense primer used was oligo 5'-GACTCGAGTC-GACAACGTT(T)$_{16}$-3' (SEQ ID NO:11) and the sense primer from the 3' end coding sequence of Kell cDNA was 5'-ATGGGGAGACTGTCCTG-3' (SEQ ID NO:12).

A PCR product of about 400 bp was obtained and was subcloned and sequenced. The 3' end sequences of different subclones are shown in Table I, below. The base sequences, prior to the poly A region, of cDNA clones from a human bone marrow library (top) and from peripheral blood of a person with common Kell phenotype (bottom) are shown. (A) indicates the poly A region.

TABLE I

| Clone No. | | |
|---|---|---|
| | Bone marrow cDNA library | |
| 191 | AATAAAAGCTGGCACTTGGCTTCCG-CCGGAATTC-3 kb ext | (SEQ ID NO: 29) |
| 185 | AATAAAAGCTGGCACTTGGCTTCCG (A) | (SEQ ID NO: 30) |
| 182 | AATAAAAGCTGGCACTTGGCTTCC (A) | (SEQ ID NO: 31) |
| 190 | AATAAAAGCTGGCACTTGGCTTC (A) | (SEQ ID NO: 32) |
| | Peripheral blood | |
| 23 | AATAAAAGCTGGCACTTGG (A) | (SEQ ID NO: 33) |
| 22 | AATAAAAGCTGGCACTTGGCTTCC (A) | (SEQ ID NO: 34) |
| 19 | AATAAAAGCTGGCACTTGGCTTCCGCTTGTCTCT (A) | (SEQ ID NO: 35) |
| 21 | AATAAAAGCTGGCACTTGGCTTCCGCTTGTCTCTT (A) | (SEQ ID NO: 36) |

The 3' end sequences of four different subclones, obtained from peripheral blood are shown in the bottom portion of Table I. All four of the subclones had identical sequences from the termination codon to the polyadenylation signal (AATAAA). At the 3' end, the base sequences differ slightly in length before the start of the poly A sequence. The distance between the polyadenylation signal and the cleavage site is known to be variable (Ref. 55). Similar variations in 3' end sequences were observed in 3 different Kell cDNAs obtained from a human bone marrow cDNA library (Clones 185, 182 and 190).

Only one of the cDNA clones, the original full-length cDNA obtained from the bone marrow library (Clone 191), contained a large 3' untranslated region. The 3 kb untranslated fragment from this cDNA clone does not hybridize with human genomic DNA indicating that it is foreign DNA. This foreign fragment is preceded by an EcoRI site and a possible liner and may have been artificially inserted during the preparation of the library.

Sequences of the 3' segments of transcripts in peripheral blood by RNA PCR only detected short 3' untranslated regions, which varied slightly in length before the poly A tail. Similar sequences were obtained when other cDNAs from the human bone marrow library were analyzed. The larger Kell transcripts could not be amplified using the RNA PCR method because of their length, but Northern analysis indicates their presence. The occurrence of multiple transcripts with larger 3' untranslated region is not uncommon and although their function is not well understood, the 3' untranslated regions are thought to play roles in regulation of expression (Refs. 56–57).

Examples 5–7

DNA Preparation

In Examples 5–7, DNA was prepared from peripheral blood obtained from persons whose Kell phenotypes have been determined serologically. DNA was prepared either from 1 to 5 ml of whole blood collected with anticoagulants or, when red cells were removed by centrifugation at 1000× g for 10 mins, from the resulting buffy coat. In both cases the procedure described by John et al. (Ref. 58) to prepare DNA was used. Some of the DNA samples were obtained from Canadian Hutterites and serological studies of these families indicated that they were homozygous for either K1 or K2. In these samples DNA was isolated as described by Zelinski et al. (Ref. 59).

Polymerase Chain Reaction

For Examples 5–7, the polymerase chain reaction was performed as follows: Denaturation, annealing and polymerization steps were performed in an automated thermocycler (Minicycler, MJ Research Inc., Watertown, Mass.). An initial cycle of 94° C. for 3 min., 62° C. for 1 min., and 72° C. for 30 seconds. In cycles 2 through 30 the conditions were 94° C. for 30 seconds, 62° C. for 30 seconds, and 72° C. for 30 seconds. In the last cycle the polymerization step at 72° C. was extended to 10 minutes. The final concentrations of reagents were 50 mM KCl, 10 mM Tris-HCl (pH 9.0), 3 mM $MgCl_2$, 350 nM of each primer, 200 µM of each dNTP, 0.1% Triton-X100, 100–200 ng genomic DNA and 2.5 units of taq polymerase in a final volume of 100 µL. The "hot start" method using Ampliwax™ from Perkin Elmer (Branchburg, N.J.) was employed. The amplified PCR products were separated by electrophoresis on 0.8% agarose gels and detected by ethidium bromide staining.

Restriction Enzyme Digestion

BsmI was added directly to the final PCR reaction mixture. The PCR mixture (10 µL) was optimized by BsmI digestion by adding 2 µL of 35 mM $MgCl_2$, 1 µL of 10 mM mercaptoethanol or 10 mM DTT, 1 µL of 10X BsmI buffer, 4 µL of water, and 2 µL of 5 units/mL BsmI. The mixture were incubated for 90 min. at 65° C. The DNA in the reaction mixture was analyzed by electrophoresis in 0.8% agarose.

Other Reagents

Taq DNA polymerase and dNTPs were purchased from Promega Co. (Madison, Wis.). X-Gal was purchased from Appligene Inc. (Pleasanton, Calif.). The DNA 1 kb ladder standards, DH5αF' strain *E. coli* competent cells, and the low melting agarose were purchased from Bethesda Research Laboratories (Gaithersburg, Md.). T4 DNA ligase and BsmI were purchased from New England Biolabs (Beverly, Mass.). pT7 blue (R) plasmid vector was purchased from Novagen (Madison, Wis.). Quick Spin™ Column (G-50 Sephadex) for DNA purification was purchased from Boehringer Mannheim, Inc. (Indianapolis, Ind.).

Example 5

Comparison of K1 and K2 DNA Sequences

Nine pairs of forward and reverse primers were used to amplify the 19 KEL exons. These primer pairs were selected to cover the open reading frames of the exons. The sequences of the primers and the target exons (spanning regions) are shown in Table II.

TABLE II

Primers Used in PCR of KEL Exons

| PCR | Primers | SEQ ID NOS: | Target Exons | Product (kb) |
|---|---|---|---|---|
| 1 | 5'-CAG TCC TCC GAA TCA GCT CCT AGA-3' | 13 | 1* 2* | 0.48 |
|   | 5'-CTC TTG GCT CCA GAG AGT TCC CAT-3' | 14 | | |
| 2 | 5'-GAA GGT GGG GAC CAA AGT GAG GAA-3' | 15 | 2*, 3, 4 | 1.0 |
|   | 5'-ACA GGG TTT GGA GCA GTC ATG GTC-3' | 16 | | |
| 3 | 5'-TTT AGT CCT CAC TCC CAT GCT TCC-3' | 4 | 5, 6 | 0.74 |
|   | 5'-TAT CAC ACA GGT GTC CTC TCT TCC-3' | 5 | | |
| 4 | 5'-ATA TTC CCC ACC TCC CCA CAC CTG-3' | 17 | 7, 8, 9 | 0.8 |
|   | 5'-ATC TAC GGT GCT CAG GCT CTC CTC-3' | 18 | | |
| 5 | 5'-GGA AGC ATG GGA GTG AGG ACT AAA-3' | 19 | 10 | 1.2 |
|   | 5'-TGG CAT CCA TGG TAC CTC ATG GAA-3' | 20 | | |
| 6 | 5'-GAG GCT TTT GAA ACC CCA GGA TGA-3' | 21 | 11 | 1.3 |
|   | 5'-TTC CCC AGC CAC CTG CCA TCT CAT-3' | 22 | | |
| 7 | 5'-CCC TTT TCC AAG GGT CAG AAG CTG-3' | 23 | 12, 13, 14, 15 | 1.4 |
|   | 5'-GGG CTT ATT TGA CCC CCA GAA TCT-3' | 24 | | |
| 8 | 5'-CCT AAT CCC TGG ATG CCT GCC TGT-3' | 25 | 14*, 15, 16, 17, 18 | 1.5 |
|   | 5'-CAG TGA GGA CAT CTG CAG AAG AGG-3' | 26 | | |
| 9 | 5'-TCC TGT GGA CCC TCC CCC TTC AAT-3' | 27 | 19* | 0.33 |
|   | 5'-GGG CGG AAG CCA AGT GCC AGC TTT T-3' | 28 | | |

The first primer is the forward sequence and the second is the antisense primer. The 2G bases at the 5' end of antisense primer of PCR are not in the gene and were added to create an SmaI site for another purpose. Some PCR products did not cover the entire exons and those exons are marked with asterisks. The PCR products of exons 1 (PCR1) and 19 (PCR 9) contain the entire translated regions. Exon 2 was spanned by overlapping PCR products (PCR 1 & 2) and exon 14 was covered by PCR 7.

Figure 5:
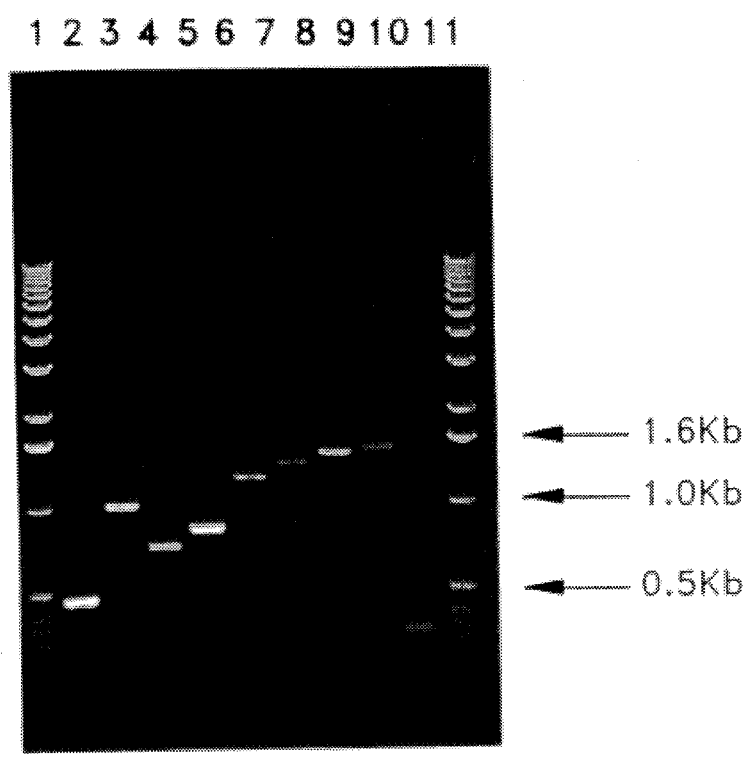
FIG. 5 shows an ethidium bromide/agarose gel illustrating a differential separation of amplified DNA corresponding to specific fragments of the Kell gene.

Genomic DNA from a homozygous K1 person was used as template DNA. The PCR products were separated by electrophoresis on 0.8% agarose gels and stained with ethidium bromide. In all cases single products ranging in size from 0.48 to 1.5 kb were obtained. FIG. 5 illustrates the PCR amplification of the KEL exons. Lanes 1 and 11 in FIG. 5 are 1 kb DNA ladder standards. Lanes 2 to 10 contain PCR products of the primer pairs PCR 1, 2, 3, 4, 5, 6, 7, 8 and 9, in that order.

Example 6

The PCR products obtained in Example 1 were sequenced using the following protocol: The PCR products, separated by electrophoresis on low 2.8% melting agarose, were eluted, ligated to pT7 Blue(R) plasmid vector and transformed in DH5αF' strain of *E. coli*. Plasmid DNA was prepared on a small scale by the alkali lysis method and purified with a Quick Spin™ (Sephadex G50) column. Standard molecular biology procedures were employed, such as are described in detail in Sambrook et al. (Ref. 36), the disclosure of which is incorporated by reference herein. DNA sequencing was performed by an automated system (Applied Biosystems, Model 373A, Version 1.2.0).

The sequenced products were compared to the previously described sequence of K2 cDNA (Ref. 24). It was unexpectedly found that the sequence of K1 DNA encodes an amino acid sequence identical to that of K2 DNA, except for a single base change. This difference between K1 and K2 occurs as a shift from C to T at nucleotide 701 in exon 6.

Figure 6:
FIG. 6 shows a comparison of corresponding portions of K1 DNA and K2 DNA.

The PCR product PCR3 (See Table II), which spans exons 5 and 6, had a single base difference when compared to K2 DNA. The base sequences of a portion of exon 6 including the K1/K2 locus, and the amino acids which they encode, are shown in FIG. 6. The sequence of K2 DNA is on the top and K1 DNA on the bottom. In the PCR3 product, which was 740 bp in length, there was a single cytosine (C) to thymine (T) substitution, corresponding to position 701 of the Kell cDNA. The C to T substitution is marked in bold letters and is highlighted with an arrow. This change predicts a threonine to methionine change at a consensus N-glycosylation site (Asn.X.Thr). An N-linked glycosylation motif in K2, and the disrupted motif in K1, are underlined. Since this single base change was the only difference between K1 and K2 encoding a change in an amino acid, this observation suggested that the threonine to methionine change (Thr→Met) at position 193 would prevent N-glycosylation at asparagine 191 in proteins expressing K1, thus identifying the K1/K2 polymorphism.

Example 7

Confirmation of K1/K2 Polymorphism by BsmI Analysis

The C to T substitution at nucleotide position 701 (nt 701) in exon 6 creates a new sequence including the sequence 5'-GAATGCT-3', which is known to define a restriction enzyme site specific for BsmI. As a result, treatment of the 740 bp PCR product which spans exons 5 and 6 (PCR3) with BsmI was hypothesized to provide a means by which to differentiate K1/K2 genotypes. In a PCR method employing digestion with BsmI, the K1/K1 genotype should yield 2 fragments, of 540 and 200 bp; the K2/K2 genotype should yield the uncut 740 bp PCR product and K1/K2 heterozygotes should yield 3 fragments of 740, 540 and 200 bp. To confirm that this base change does in fact identify the K1 genotype, this region was analyzed in 42 different persons of known K1/K2 phenotype.

The PCR3 primer pair (Table II) was used to generate PCR products (740 bp) by PCR amplification of DNA obtained from various Kell phenotypes. After amplification, the samples were treated with BsmI and separated by electrophoresis on 0.8% agarose gels.

Figure 7:
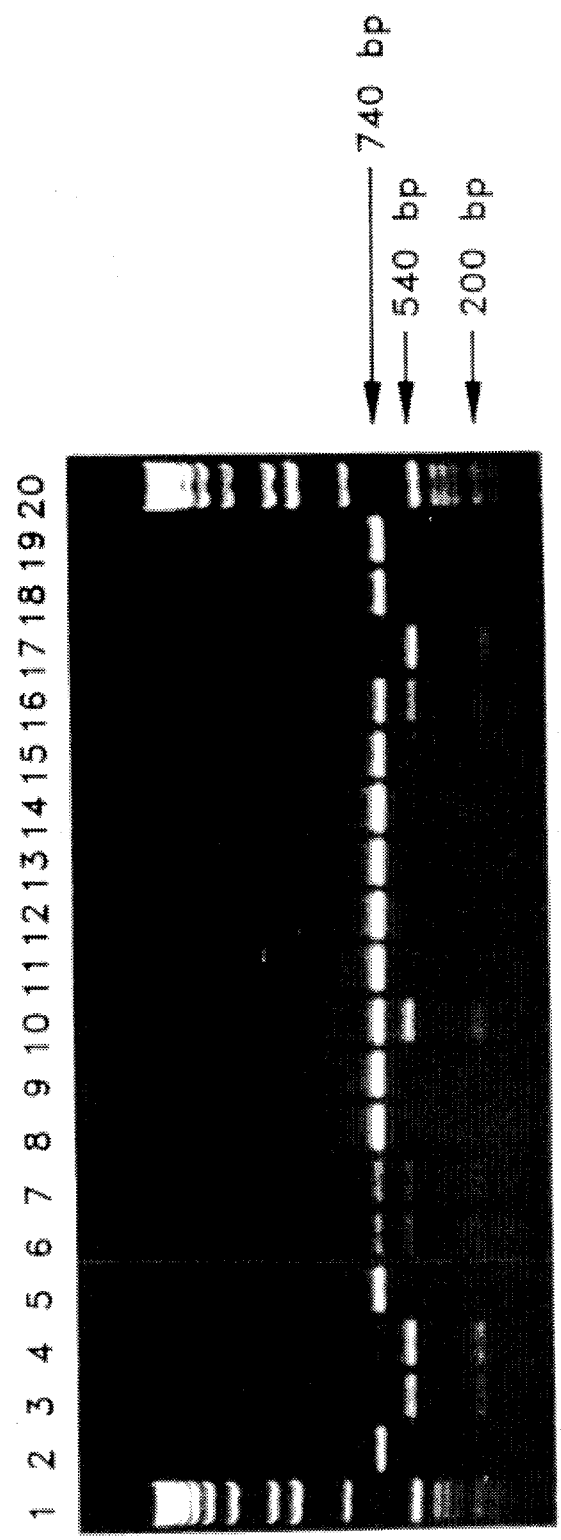
FIG. 7 shows an ethidium bromide/agarose gel illustrating a differential separation of amplified DNA corresponding to K1 DNA and K2 DNA according to the method of the invention.

FIG. 7 illustrates the results obtained in the above-described experiment. The gel lanes are defined in Table III, below:

TABLE III

| Lane | Phenotype | Lane | Phenotype |
| --- | --- | --- | --- |
| 1 | DNA Standard | 11 | K:−1, 2, 3, −4 |
| 2 | Untreated PCR3 | 12 | K:−1, 2, 6, −7 |
| 3 | K:1, −2 | 13 | McLeod |
| 4 | K:1, −2 | 14 | K:−1, 2, 10 |
| 5 | K:−1, 2 | 15 | K:−1, 2, 14, 24 |
| 6 | K:1, 2 | 16 | K:1, 2 |
| 7 | K:1, 2 | 17 | K:1, −2 |
| 8 | K:−1, 2 | 18 | K:−1, 2 |
| 9 | $K_o$ | 19 | K:−1, 2 |
| 10 | K:1, 2 | 20 | DNA Standard |

In FIG. 7, lanes 1 and 20 contain 1 kb ladder DNA standards. Lane 2 is untreated PCR3 from K1 homozygotes. Lanes 3 to 19 are treated with BsmI. All K2 homozygote (K:−1,2) samples gave uncut 740 bp products. K1 homozygotes (K:1,−2) yielded only 540 and 200 bp fragments. K1/K2 heterozygotes (K:1,2) had 3 bands, the uncut 740 and the smaller 540 and 200 bp products.

Of the 42 DNA samples tested, 12 were either K1 or K2 homozygotes, 6 were K1/K2 heterozygotes and 24 were K:−1,2 phenotypes, but contained low prevalence or rare Kell phenotypes. These included K3, K6, K10, $K_o$, K14/K24 heterozygote, and a McLeod phenotype. In 40 of the 42 cases the BsmI genotyping agreed with the Kell phenotypes which were determined by serological analysis of red cells. In two cases, genotyping identified one of the samples as K:−1,2 homozygote and the other as a K:1,2 heterozygote. These two samples were, however, serologically identified as having "weak" K1 phenotypes.

None of the other low prevalence or rare Kell phenotypes listed above had the C to T base substitution in exon 6, indicating that this change is specific for the K1/K2 polymorphism.

Example 8

In a method of differentially determining K1/K2 genotype, the polymerase chain reaction was employed to test samples of genomic DNA using a unique primer mixture. The primer mixture included the following primers:

TABLE IV

| MK1R | ATA CTG ACT CAT CAG AAG TTT CAG CA | (SEQ ID NO: 1) |
| MK2F | TGG ACT TCC TTA AAC TTT AAC TGA AC | (SEQ ID NO: 3) |
| EI5F | TTT AGT CCT CAC TCC CAT GCT TCC | (SEQ ID NO: 4) |
| EI6R | TAT CAC ACA GGT GTC CTC TCT TCC | (SEQ ID NO: 5) |

The MK1R primer is specific for K1 DNA, producing a PCR product 540 bp in length. The MK2F primer is specific for K2 DNA, and produces a PCR product 240 bp in length. The other primers EI5F and EI6R are K1/K2 specific, producing PCR products 740 bp in length, and are used as an internal control.

The primer mix included the primers in the following concentrations: 20 ng/μL MK1R; 20 ng/μL MK2F; 30 ng/μL EI5F; and 30 ng/μL EI6R. EI5F and EI6R primers are used in the PCR for two reactions, while the MK1R and MK2F primers are each used for only one reaction. The concentrations of the primers were adjusted to ensure sufficient quantities of the EI5F and EI6R primers for the duration of the reaction.

Blood samples were obtained from human volunteers. DNA was isolated from leukocytes present in the buffy coat of blood samples using the method described elsewhere herein.

Reaction tubes were set up including one Ampliwax™ and 25 μL of a first reagent cocktail including: 2.5 μL 10X buffer (Promega Co., Madison, Wis.); 4 μL dNTP; 3 μL 25 mm MgCl$_2$; 7 μL primer mix; and 8.5 μL H$_2$O, to give a preliminary reaction mixture volume of 25 μL. These preliminary mixtures were incubated a 80° C. for 5 min. and cooled to room temperature for 5 min. before proceeding. To each of the tubes were added 23 μL of a second reagent cocktail including: 2.5 μL 10X buffer; 3 μL 25 mM MgCl$_2$; 17 μL H$_2$O; and 0.5 μL taq DNA polymerase (Promega Co., 5 units/μL) and 100 ng of isolated genomic DNA in 2 μL H$_2$O.

The PCR reaction was performed using the following cycling program. The initial cycle comprised 94° C. for 3 minutes, 62° C. for 1 minute, and 72° C. for 30 seconds. Cycles 2–30 each included 94° C. for 30 seconds, 62° C. for 30 seconds, and 72° C. for 30 seconds. In the last cycle, the polymerization step was 72° C. was extended to 10 minutes.

Following completion of the PCR, the amplified products were resolved using ethidium bromide/agarose gel electrophoresis as described in the art.

Figure 8:
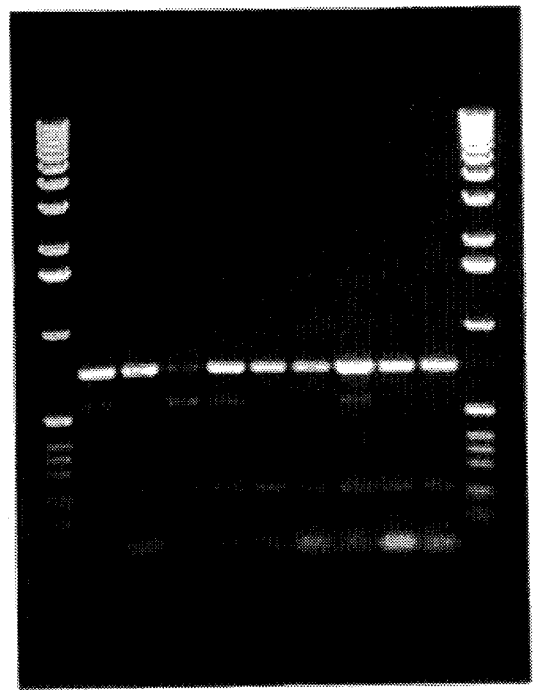
FIG. 8 shows an ethidium bromide/agarose gel electrophoresis resolution of PCR products obtained according to the method of the invention.

The results are of this procedure are shown in FIG. 8. Lanes 1 and 11 are identical control samples including mixed DNA fragments of known size. Lanes 2–4 represent internal control samples from subjects in whom the K1/K2 genotype was already known. Control Lane 2 shows the presence of 540 bp and 740 bp fragments, indicating that the subject is homozygous K1 (K:1,–2). Control Lane 3 shows the presence of 200 bp and 740 bp fragments, indicating that the subject is homozygous K2 (K:–1,2). Control Lane 4 shows the presence of each of the K1/K2 fragments, i.e., 200 bp, 540 bp, and 740 bp, indicating that the subject is heterozygous (K:1,2).

Lanes 5–7 in FIG. 8 represent samples from a family of test subjects: Lanes 5 and 6 represent parents and Lane 7 represents the fetus. A comparison of the test bands with the control bands reveals that the parent represented in Lane 5 is heterozygous (K:1,2) and that the parent represented in Lane 6 is homozygous K2 (K:–1,2). The fetus is clearly homozygous K2 (K:–1,2).

Lanes 8–10 in FIG. 8 represent samples from another family of test subjects. The first parent, represented in Lane 8, is heterozygous (K:1,2), while the second parent, represented in Lane 9, is homozygous K2 (K:–1,2). The fetus, represented in Lane 10, is identifiable as being homozygous K2 (K:–1,2).

The experimental data provided in Examples 7 and 8 clearly demonstrate the diagnostic efficacy of the method of the invention. The examples show that individuals of each of the three K1/K2 genotypes can be distinguished positively by virtue of the differences between K1 DNA and K2 DNA. More particularly, the newly identified locus of K1/K2 polymorphism can be exploited by means of amplification of Kell DNA using K1 and K2 specific nucleic acid probes, as well as by differential digestion of K1/K2 DNA with a restriction enzyme.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

REFERENCES

1. Giblett ER, "A critique of the theoretical hazard of inter- vs. intra-racial transfusion" *Transfusion* 1:233 (1961).
2. Mayne KM, Bowell PJ, and Pratt GA, "The significance of anti-Kell sensitization in pregnancy" *Clin Lab Haematol* 12:379–385 (1990).
3. Duguid JKM, and Bromilow IM, "Haemolytic disease of the newborn due to anti-K" *Vox Sang* 58:69 (1990).
4. Moncharmont P, Juron-Dupraz F, Doillon M, Vignal M, and Debeaux V, "A case of hemolytic disease of the newborn infant due to anti-K (Cellano)" *Acta Haematol* 85:45 (1991).
5. Constantine G, Fitzgibbon N, and Weave JB, "Anti-Kell in pregnancy" *Brit J Obs Gyn* 98:943 (1991).
6. Leggat HM, Gibson JM, Barron SL, and Reid MM, "Anti-Kell in pregnancy" *Brit J Obs Gyn* 98:162 (1991).
7. Bowman JM, Pollock JM, Manning FA, Harman CK, and Menticoglou S, "Maternal Kell blood group alloimmunization" *Obstetrics and Gynecology* 79:239 (1992).
8. Marsh WL, "Blood groups of human red cells in clinical practice of blood transfusion" (Petz, LD and Swisher SN, eds) pp. 79–130, Churchill-Livingstone, New York (1981).
9. Marsh WL and Redman CM, "Recent developments in the Kell blood group system" *Trans Med Rev* 1:4 (1987).
10. Marsh WL and Redman CM, "The Kell blood group system: a review" *Transfusion* 30:151 (1990).
11. Redman CM and Marsh WL, "The Kell antigens and McLeod red cells" in *Protein Blood Group Antigens of the Human Red Cell: Structure, Function and Clinical Significance*. (Agre PC and Cartron JP, eds.) pp 53–69, Johns Hopkins University Press, Baltimore, Md. (1992).
12. Redman CM and Marsh WL, "The Kell blood group system and the McLeod phenotypes" *Seminars in Hematology* 40:309 (1993).
13. Petty AC, Daniels GL, and Tippett P, "Application of the MAIEA assay to the Kell blood group system" *Vox Sang* 66:216 (1994).
14. Lee S, Zambas E, Marsh WL, and Redman CM, "The human Kell blood group gene maps to chromosome 7q33 and its expression is restricted to erythroid cells" *Blood* 81:2804 (1993).
15. Zelinski T, Coghlan G, Myal Y, Shiu RPC, Phillips S, White L, and Lewis M, "Genetic linkage between the Kell blood group system and prolactin-inducible protein loci: Provisional assignment of KEL to chromosome 7" *Ann Hum Genet* 55:137 (1991).
16. Purohit KR, Weber JL, Ward LJ, and Keats BJB, "The Kell blood group locus is closed to the cystic fibrosis locus on chromosome 7" *Hum Genet* 89:457 (1992).

17. Murphy MT, Morrison N, Miles JS, Fraser RH, Spurr NK, and Boyd E, "Regional chromosomal assignment of the Kell blood group locus (KEL) to chromosome 7q35-q35 by fluorescence in situ hybridization: Evidence for the polypeptide nature of antigenic variations" *Hum Genet* 91:585 (1993).

18. Redman CM, Marsh WL, Mueller KA, Avellino GP, and Johnson CL, "Isolation of Kell-active protein from the red cell membrane" *Transfusion* 24:176 (1984).

19. Wallas C, Simon R, Sharpe MA, and Byler C, "Isolation of Kell-reactive protein from red cell membranes" *Transfusion* 26:173 (1986).

20. Redman CM, Avellino G, Pfeffer SR, Mukherjee TK, Nichols M, Rubinstein P, and Marsh WL, "Kell blood group antigens are part of a 93,000 Dalton red cell membrane protein" *J Biol Chem* 261:9521 (1986).

21. Jaber A, Blanchard D, Goossens D, Bloy C, Lambin P, Rouger P, Salmon C, and Cartron JP, "Characterization of blood group Kell (K1) antigen with a human monoclonal antibody" *Blood* 73:1597 (1989).

22. Jaber A, Loirot MJ, Willem C, Bloy C, Cartron JP, and Blanchard D, "Characterization of murine monoclonal antibodies directed against the Kell blood group glycoprotein" *Brit J Haematol* 79:311 (1991).

23. Parson SF, Gardner B, and Anstee DJ, "Monoclonal antibodies against Kell glycoprotein: Serology, immunochemistry and quantification of antigen sites" *Transfusion Medicine* 3:137 (1993).

24. Lee S, Zambas E, Marsh WL, and Redman CM, "Molecular cloning and primary structure of Kell blood group protein" *Proc Natl Acad Sci (USA)* 88:6353 (1991).

25. Redman CM, Lee S, Ten Bokkel Huinink D, Rabin, BI, Johnson CL, Oyen R and Marsh WL, "Comparison of human and chimpanzee Kell blood group system" *Transfusion* 239:486–490 (1989).

26. Branch D, Muensch H, Sy Siok Hian A, and Petz D, "Disulfide bonds are a requirement of Kell and Cartwright (Yt$^a$) blood group antigen integrity" *Br J Haematol* 54:573–578 (1993).

27. Bause E, "Structural requirements of N-glycosylation proteins" *Biochem J* 209:331–336 (1983).

28. Telen MJ, Le Van Kim C, Guizzo ML, Cartron JP, and Colin Y, "Erythrocyte Webb-type glycophorin C variant lacks N-glycosylation due to an asparagine to serine substitution" *Am J Hematol* 37:51–52 (1991).

29. Chang S, Reid M, Conboy J, Kan Y, and Mohandas N, "Molecular characterization of erythrocyte glycophorin C variants" *Blood* 77:644–648 (1991).

30. Innis MA, Gelfand DH, Sninsky JJ, and White TJ, *PCR Protocols: A Guide to Methods and Applications,* Academic Press, Inc., San Diego (1990).

31. Landegren U, et al., *Science* 241:1077 (1988).

32. Barany F, *PCR Methods and Applications* 1:5 (1991).

33. Narang et al., *Meth Enzymol* 68:90 (1979).

34. Brown et al., *Meth Enzymol* 68:109 (1979).

35. Beaucage et al., *Tetrahedron Lett* 22:1859 (1981).

36. Sambrook J, Fritsch EF, and Maniatis T, *Molecular Cloning: A Laboratory Manual,* 2d. ed. Cold Spring Harbor Laboratory, NY (1989).

37. Lee S, Zambas E, Green ED, and Redman C, "Organization of the gene encoding the human Kell blood group protein" *Blood* in press.

38. Jongeneel CX, Bouvier J, and Bairoch A, "A unique signature identifies a family of zinc-dependent metallopeptidases" *FEBS Letters* 242:211 (1989).

39. Gerard NP, Bao L, Yiao-Ping H, Eddy RL, Shows TB, and Gerard C, "Characterization of the human C5a receptor gene" *Biochemistry* 32:1243 (1993).

40. Letarte M, Vera R, Tran JBL, Addis JBL, Ouizuka RJ, Quackenbush EJ, Jongeneel CY, and McInnes RR, "Common acute lymphocytic leukemia antigen is identical to neutral endopeptidase" *J Exp Med* 168:1247 (1988).

41. Shipp MA, Vijayaraghavan J, Schmidtt EV, Masteller EL, D'Adamio L, Heish LB, and Reinherz EL, "Common acute lymphoblastic antigen (CALLA) is active neutral endopeptidase 24.11 (enkephalinase): Direct evidence by cDNA transfection analysis" *Proc Natl Acad Sci USA* 86:297 (1989).

42. D'Adamio L, Shipp MA, Masteller EL, and Reinherz EL, "Organization of the gene encoding common acute lymphoblastic leukemia antigen (neutral endopeptidases 24.11):Multiple mini exons and separate 5' untranslated region" *Proc Natl Acad Sci USA* 86:7103 (1989).

43. Bucher P, and Trifonov EN, "Compilation and analysis of eukaryotic POL II promoter sequences" *Nucleic Acids Res.* 14:10009 (1986).

44. Evans T, Reitman M, and Felsenfeld G, "An erythrocyte-specific DNA-binding factor recognizes a regulatory sequence common to all chicken globin genes" *Proc Natl Acad Sci, USA* 85:5976 (1988).

45. Plum M, Frampton J, Wainwright H, Walker M, Macleod K, Goodwin G, and Harrisson P, "GATAAG: A cis-control region binding an erythroid specific nuclear factor with a role in globin and non-globin gene expression" *Nucleic Acids Res.* 17:73 (1989).

46. Philipsen S, Talbot D, Fraser P, and Grosvelt F, "The β-globin dominant control region: Hypersensitive site 2" *EMBO J.* 9:2159 (1990).

47. Beaupain D, Elouet JF, and Romeo PH, "Initiation of transcription of erythroid promoter of the porphobilinogen deaminase gene is regulated by a cis-acting sequence around the cap site" *Nucleic Acids Res.* 18:6509 (1990).

48. Maouche L, Tournamille C, Hattab C, Boffa G, Cartron JP, and Chretian S, "Cloning of the gene encoding the human erythropoietin receptor" *Blood* 78:2557 (1991).

49. Rahuel C, Vinit M-H, Lemarchandel V, Cartron JP, and Romeo P-H, "Erythroid specific activity of the glycophorin B promoter requires GATA-1 mediated displacement of a repressor" *EMBO J.* 11:4095 (1992).

50. Cherif-Zahar B, LeVan Kim C, Rouillac C, Raynal V, Cartron JP, and Colin YP, "Organization of the gene (RHCE) encoding the human blood group RhCcEe antigens and characterization of the promoter region" *Genomics* 19:68 (1994).

51. Crotta S, Nicolis S, Ronchi A, Ottolenghy S, Ruzzi L, Shimada Y, Migliaccio AR, and Migliaccio G, "Progressive inactivation of the expression of the erythroid transcription factor in GM- and G-CSF-dependent cell lines" *Nucleic Acid Res.* 18:6864 (1990).

52. Orkin SH, Tsai SF, Zan LI, Martin D, and Whitelaw E, "The erythroid-specific transcription factor GATA-1: Structure and expression" in *Regulation of Hemoglobin Switching,* (Stamatoyannopoulus G, Nienhuis AW, eds) Alan R Liss, New York. pp 310 (1992).

53. Crossley M, and Orkin SH, "Regulation of the β globin locus" *Current Opinion in Genetics and Development* 3:232 (1993).

54. Goosens M and Kan YW, "DNA analysis in the diagnosis of hemoglobin disorders" *Methods Enzymol* 76:805 (1981).

55. Wahle E and Keller W, "The biochemistry of 3' end cleavage and polyadenylation of messenger RNA precursors" *Ann Rev Biochem* 61:419 (1992).

56. Rastinejad F and Blau HM, "Genetic complementation reveals a novel regulatory role for 3' untranslated regions in growth and differentiation" *Cell* 72:903 (1993).

57. Jackson RJ, "Cytoplasmic regulation of mRNA function:The importance of the 3' untranslated region" *Cell* 74:9 (1993).
58. John SWM, Weitzner G, Rozen R, and Scriver CR, "A rapid procedure for extracting genomic DNA from leukocytes" *Nucleic Acids Res* 19:408 (1991).
59. Zelinski T, "The use of DNA restriction fragment length polymorphisms in conjunction with blood group serology" *Transfusion* 31:762–770 (1991).
60. Glick BR, and Pasternak JJ, *Molecular Biotechnology: Principles and Applications of Recombinant DNA* ASM Press, Washington, D.C. (1994).

What is claimed is:

1. A diagnostic method for the differential determination of K1 and/or K2 genotype in a patient, comprising:
amplifying a DNA sample obtained from a patient using a primer which amplifies only K1 DNA and/or K2 DNA, including the locus which determines K1/K2 polymorphism, to identify the presence of amplified DNA corresponding to K1 DNA and/or K2 DNA.

2. The diagnostic method of claim 1, wherein said primer amplifies K1 DNA and K2 DNA.

3. The diagnostic method of claim 1, wherein said primer comprises at least one primer which amplifies only K1 DNA.

4. The diagnostic method of claim 1, wherein said primer comprises at least one primer which amplifies only K2 DNA.

5. The diagnostic method of claim 1, wherein said primer comprises at least one primer which amplifies only K1 DNA and at least one primer which amplifies only K2 DNA.

6. The diagnostic method of claim 1, wherein said primer includes a primer specific for K1 comprising a nucleotide sequence selected from the group consisting of: ATA CTG ACT CAT CAG AAG TTT CAG CA (SEQ ID NO:1), and ATA CTG ACT CAT CAG AAG TCT CAG CA (SEQ ID NO:2).

7. The diagnostic method of claim 1, wherein said primer includes a primer specific for K2 comprising the nucleotide sequence: TGG ACT TCC TTA AAC TTT AAC TGA AC (SEQ ID NO:3).

8. The diagnostic method of claim 1, wherein said primer includes a primer specific for K1 DNA and/or K2 DNA comprising a nucleotide sequence selected from the group consisting of: TTT AGT CCT CAC TCC CAT GCT TCC, (SEQ ID NO:4), and TAT CAC ACA GGT GTC CTC TCT TCC, (SEQ ID NO:5).

9. The diagnostic method of claim 1, wherein said amplifying includes amplifying by polymerase chain reaction, ligase chain reaction or a combination thereof.

10. The diagnostic method of claim 1, wherein said method further comprises digesting said DNA using a restriction enzyme which differentially cleaves K1 DNA and K2 DNA.

11. The diagnostic method of claim 10, wherein said digesting follows said amplifying.

12. The diagnostic method of claim 10, wherein said digesting precedes said amplifying.

13. The diagnostic method of claim 10, wherein said restriction enzyme is BsmI.

14. The diagnostic method of claim 1, wherein said method further comprises:
separating said amplified DNA according to molecular weight to form a pattern of fragments,
wherein said pattern of fragments provides specific information diagnostic of the K1/K2 genotype of the patient.

15. The diagnostic method of claim 1, wherein said DNA sample is obtained from a biological sample containing erythroid tissue of the patient.

16. The diagnostic method of claim 15, wherein said biological sample comprises amniotic fluid and wherein said patient is a fetus in utero.

17. The diagnostic method of claim 15, wherein said biological sample comprises a blood sample.

18. The diagnostic method of claim 1, further comprising serologically typing a blood sample from said patient to determine Kell phenotype.

19. A nucleic acid oligomer comprising a nucleic acid sequence which specifically binds to a region of Kell DNA diagnostic of K1 DNA and/or K2 DNA.

20. The nucleic acid oligomer of claim 19, wherein said region of Kell DNA is specific to K1 DNA.

21. The nucleic acid oligomer of claim 19, wherein said region of Kell DNA is specific to K2 DNA.

22. The nucleic acid oligomer of claim 19, wherein said nucleic acid sequence is detectably labeled.

23. The nucleic acid oligomer of claim 19, wherein said nucleic acid sequence is attached to a substrate.

24. The nucleic acid oligomer of claim 19, wherein said nucleic acid sequence is exactly complementary to said region of Kell DNA.

25. A nucleic acid oligomer having a nucleic acid sequence which encodes a portion of K1 protein including the K1 domain.

26. The nucleic acid oligomer of claim 25, wherein said region of Kell DNA is specific to K1 DNA.

27. The nucleic acid oligomer of claim 25, wherein said region of Kell DNA is specific to K2 DNA.

28. The nucleic acid oligomer of claim 25, wherein said nucleic acid sequence is detectably labeled.

29. The nucleic acid oligomer of claim 25, wherein said nucleic acid sequence is attached to a substrate.

30. The nucleic acid oligomer of claim 25, wherein said nucleic acid sequence is exactly homologous to said region of Kell DNA.

31. A nucleic acid primer comprising a primer which specifically binds to or causes elongation through K1 DNA and/or K2 DNA.

32. The nucleic acid primer of claim 31, wherein said primer specifically binds to or causes elongation through K1 DNA.

33. The nucleic acid primer of claim 31, wherein said primer specifically binds to or causes elongation through K2 DNA.

34. The nucleic acid primer of claim 31, wherein said primer comprises a K1 primer which specifically binds to or causes elongation through K1 DNA and a K2 primer which specifically binds to or causes elongation through K2 DNA.

35. An isolated Kell-based polypeptide, which is specifically reactive with an anti-K1 antibody.

36. The isolated Kell-based polypeptide of claim 35, wherein said polypeptide is detectably labeled.

37. The isolated Kell-based polypeptide of claim 35, wherein said polypeptide is attached to a substrate.

38. The isolated Kell-based polypeptide of claim 35, wherein said polypeptide has an amino acid sequence which includes a methionine residue at a position corresponding to amino acid 192 of the Kell protein.

39. The isolated Kell-based polypeptide of claim 35, wherein said polypeptide has an amino acid sequence identical to at least a portion of the Kell protein including the K1 domain.

40. A diagnostic method for detecting alloimmunization of a patient to K1 antigen, comprising:

measuring a parameter of immune reactivity of a blood sample of a patient with a peptide probe, wherein said peptide probe comprises an amino acid sequence which is specifically reactive with anti-K1 antibodies in the sample.

41. The diagnostic method of claim 40, wherein said amino acid sequence is exactly complementary to said region of the K1 domain of the Kell protein.

42. A diagnostic method for the detection of a target nucleic acid encoding at least a part of the K1 or K2 domain of a Kell protein, comprising:

ascertaining the presence, in a nucleic acid fraction obtained from a patient, of a target nucleic acid encoding at least a part of the K1 or K2 domain of a Kell protein by means of a nucleic acid probe which is known to specifically bind to a nucleic acid sequence encoding the K1 or K2 domain of a Kell protein.

43. The diagnostic method of claim 42, wherein said nucleic acid probe specifically binds to a nucleic acid sequence encoding the K1 domain of Kell protein.

44. The diagnostic method of claim 42, wherein said nucleic acid probe specifically binds to a nucleic acid sequence specifically encoding the K2 domain of Kell protein.

45. The diagnostic method of claim 42, wherein said nucleic acid probe is detectably labeled.

46. The diagnostic method of claim 42, wherein said nucleic acid probe is attached to a substrate.

47. The diagnostic method of claim 42, wherein said target nucleic acid is genomic DNA.

48. The diagnostic method of claim 42, wherein the target nucleic acid is mRNA.

49. The diagnostic method of claim 42, wherein the target nucleic acid is cDNA.

50. A diagnostic kit for the differential determination of K1/K2 genotype, comprising:

(a) a primer specific for a region of K1 DNA and/or K2 DNA including the locus which determines the K1/K2 polymorphism; and (b) a container.

51. The diagnostic kit of claim 50, wherein said container comprises a biological specimen container for housing said primer.

52. A diagnostic kit for determining K1/K2 Kell blood group genotype by detecting target nucleic acid sequences specific to K1 and K2, said kit comprising:

(a) a primer set including first and second PCR primers wherein said first PCR primer is an oligonucleotide that will bind to or cause elongation through a sequence specific to K1 and said second PCR primer is an oligonucleotide that will bind to or cause elongation through a sequence specific to K2; and (b) a microtiter plate having a plurality of wells and having bound thereto oligonucleotide capture probes having a nucleic acid sequence which specifically binds to said target sequences.

53. A recombinant expression vector capable of transforming a cell to cause expression of a polypeptide including the K1 domain, comprising an expression vector which includes a nucleic acid sequence encoding at least a part of K1 protein including at least the K1 domain.

54. The recombinant expression vector of claim 53, wherein said nucleic acid sequence comprises K1 cDNA.

55. A method of producing a cell line transformed to express a K1 polypeptide or protein, comprising transforming a cell with the recombinant expression vector of claim 53 to produce a transformed cell, and establishing a stable transformed cell line derived from said transformed cell.

56. A transformed cell line produced according to the method of claim 55.

57. An isolated nucleic acid sequence encoding K1 protein, comprising K1 cDNA.

* * * * *

UNITED STATES PATENT AND TRADEMARK OFFICE
CERTIFICATE OF CORRECTION

PATENT NO. : 5,589,336
DATED : December 31, 1996
INVENTOR(S) : Lee, et al.

It is certified that error appears in the above-indentified patent and that said Letters Patent is hereby corrected as shown below:

THE TITLE PAGE:

item [75] for Inventors, now reads "Colvin Redman, Long Island, N.Y.", should read --Colvin Redman, Franklin Square, N.Y.--.

Signed and Sealed this

Sixth Day of May, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 60

( 2 ) INFORMATION FOR SEQ ID NO:1:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:1:

ATACTGACTC ATCAGAAGTT TCAGCA      26

( 2 ) INFORMATION FOR SEQ ID NO:2:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:2:

ATACTGACTC ATCAGAAGTC TCAGCA      26

( 2 ) INFORMATION FOR SEQ ID NO:3:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:3:

TGGACTTCCT TAAACTTTAA CTGAAC      26

( 2 ) INFORMATION FOR SEQ ID NO:4:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:4:

TTTAGTCCTC ACTCCCATGC TTCC 24

(2) INFORMATION FOR SEQ ID NO:5:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (ii) MOLECULE TYPE: genomic DNA (iii) HYPOTHETICAL: no (xi) SEQUENCE DESCRIPTION: SEQ ID NO:5:

TATCACACAG GTGTCCTCTC TTCC 24

(2) INFORMATION FOR SEQ ID NO:6:

(i) SEQUENCE CHARACTERISTICS:
        (A) LENGTH: 35 nucleotides
        (B) TYPE: nucleic acid
        (C) STRANDEDNESS: single
        (D) TOPOLOGY: linear (ii) MOLECULE TYPE: genomic DNA (iii) HYPOTHETICAL: no (xi) SEQUENCE DESCRIPTION: SEQ ID NO:6:

GGAGACTTCC AAGGTCTTAG CTATCACTTA AGCAC 35

(2) INFORMATION FOR SEQ ID NO:7:

(i) SEQUENCE CHARACTERISTICS:
        (A) LENGTH: 38 nucleotides
        (B) TYPE: nucleic acid
        (C) STRANDEDNESS: single
        (D) TOPOLOGY: linear (ii) MOLECULE TYPE: genomic DNA (iii) HYPOTHETICAL: no (xi) SEQUENCE DESCRIPTION: SEQ ID NO:7:

CTGGTTCGGC CCACCTCTGA AGGTTCCAGA ATCGATAG 38

(2) INFORMATION FOR SEQ ID NO:8:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (ii) MOLECULE TYPE: genomic DNA (iii) HYPOTHETICAL: no (xi) SEQUENCE DESCRIPTION: SEQ ID NO:8:

CTCGGCTCTT CCTCACTTTG GTCC 24

(2) INFORMATION FOR SEQ ID NO:9:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear ( i i ) MOLECULE TYPE: genomic DNA ( i i i ) HYPOTHETICAL: no ( x i ) SEQUENCE DESCRIPTION: SEQ ID NO:9:

CTCTTGGCTC CAGAGAGTTC CCAT 24

( 2 ) INFORMATION FOR SEQ ID NO:10:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:10:

CCCACCTTCC ATCTGTCTAT CTTC 24

( 2 ) INFORMATION FOR SEQ ID NO:11:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:11:

GACTCGAGTC GACAACGTTT TTTTTTTTT TTTTT 35

( 2 ) INFORMATION FOR SEQ ID NO:12:

( i ) SEQUENCE CHARACTERISTICS:
        ( A ) LENGTH: 17 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:12:

ATGGGGAGAC TGTCCTG 17

( 2 ) INFORMATION FOR SEQ ID NO:13:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:13:

CAGTCCTCCG AATCAGCTCC TAGA 24

( 2 ) INFORMATION FOR SEQ ID NO:14:

( i ) SEQUENCE CHARACTERISTICS:

(A) LENGTH: 24 nucleotides
(B) TYPE: nucleic acid
(C) STRANDEDNESS: single
(D) TOPOLOGY: linear (ii) MOLECULE TYPE: genomic DNA (iii) HYPOTHETICAL: no (xi) SEQUENCE DESCRIPTION: SEQ ID NO:14:

CTCTTGGCTC CAGAGAGTTC CCAT  24

(2) INFORMATION FOR SEQ ID NO:15:

(i) SEQUENCE CHARACTERISTICS:
(A) LENGTH: 24 nucleotides
(B) TYPE: nucleic acid
(C) STRANDEDNESS: single
(D) TOPOLOGY: linear (ii) MOLECULE TYPE: genomic DNA (iii) HYPOTHETICAL: no (xi) SEQUENCE DESCRIPTION: SEQ ID NO:15:

GAAGGTGGGG ACCAAAGTGA GGAA  24

(2) INFORMATION FOR SEQ ID NO:16:

(i) SEQUENCE CHARACTERISTICS:
(A) LENGTH: 24 nucleotides
(B) TYPE: nucleic acid
(C) STRANDEDNESS: single
(D) TOPOLOGY: linear (ii) MOLECULE TYPE: genomic DNA (iii) HYPOTHETICAL: no (xi) SEQUENCE DESCRIPTION: SEQ ID NO:16:

ACAGGGTTTG GAGCAGTCAT GGTC  24

(2) INFORMATION FOR SEQ ID NO:17:

(i) SEQUENCE CHARACTERISTICS:
(A) LENGTH: 24 nucleotides
(B) TYPE: nucleic acid
(C) STRANDEDNESS: single
(D) TOPOLOGY: linear (ii) MOLECULE TYPE: genomic DNA (iii) HYPOTHETICAL: no (xi) SEQUENCE DESCRIPTION: SEQ ID NO:17:

ATATTCCCCA CCTCCCCACA CCTG  24

(2) INFORMATION FOR SEQ ID NO:18:

(i) SEQUENCE CHARACTERISTICS:
(A) LENGTH: 24 nucleotides
(B) TYPE: nucleic acid
(C) STRANDEDNESS: single
(D) TOPOLOGY: linear (ii) MOLECULE TYPE: genomic DNA (iii) HYPOTHETICAL: no (xi) SEQUENCE DESCRIPTION: SEQ ID NO:18:

ATCTACGGTG CTCAGGCTCT CCTC  24

( 2 ) INFORMATION FOR SEQ ID NO:19:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:19:

GGAAGCATGG GAGTGAGGAC TAAA 24

( 2 ) INFORMATION FOR SEQ ID NO:20:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:20:

TGGCATCCAT GGTACCTCAT GGAA 24

( 2 ) INFORMATION FOR SEQ ID NO:21:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:21:

GAGGCTTTTG AAACCCCAGG ATGA 24

( 2 ) INFORMATION FOR SEQ ID NO:22:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:22:

TTCCCCAGCC ACCTGCCATC TCAT 24

( 2 ) INFORMATION FOR SEQ ID NO:23:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:23:

CCCTTTTCCA AGGGTCAGAA GCTG                                        24

( 2 ) INFORMATION FOR SEQ ID NO:24:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:24:

GGGCTTATTT GACCCCAGA ATCT                                         24

( 2 ) INFORMATION FOR SEQ ID NO:25:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:25:

CCTAATCCCT GGATGCCTGC CTGT                                        24

( 2 ) INFORMATION FOR SEQ ID NO:26:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:26:

CAGTGAGGAC ATCTGCAGAA GAGG                                        24

( 2 ) INFORMATION FOR SEQ ID NO:27:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:27:

TCCTGTGGAC CCTCCCCCTT CAAT                                        24

( 2 ) INFORMATION FOR SEQ ID NO:28:

( i ) SEQUENCE CHARACTERISTICS:
        ( A ) LENGTH: 25 nucleotides
        ( B ) TYPE: nucleic acid (C) STRANDEDNESS: single
        (D) TOPOLOGY: linear (ii) MOLECULE TYPE: genomic DNA (iii) HYPOTHETICAL: no (xi) SEQUENCE DESCRIPTION: SEQ ID NO:28:

GGGCGGAAGC CAAGTGCCAG CTTTT                                         25

(2) INFORMATION FOR SEQ ID NO:29:

(i) SEQUENCE CHARACTERISTICS:
        (A) LENGTH: 34 nucleotides
        (B) TYPE: nucleic acid
        (C) STRANDEDNESS: single
        (D) TOPOLOGY: linear (ii) MOLECULE TYPE: genomic DNA (iii) HYPOTHETICAL: no (xi) SEQUENCE DESCRIPTION: SEQ ID NO:29:

AATAAAAGCT GGCACTTGGC TTCCGCCGGA ATTC                              34

(2) INFORMATION FOR SEQ ID NO:30:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (ii) MOLECULE TYPE: genomic DNA (iii) HYPOTHETICAL: no (xi) SEQUENCE DESCRIPTION: SEQ ID NO:30:

AATAAAAGCT GGCACTTGGC TTCCG                                         25

(2) INFORMATION FOR SEQ ID NO:31:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (ii) MOLECULE TYPE: genomic DNA (iii) HYPOTHETICAL: no (xi) SEQUENCE DESCRIPTION: SEQ ID NO:31:

AATAAAAGCT GGCACTTGGC TTCC                                          24

(2) INFORMATION FOR SEQ ID NO:32:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear (ii) MOLECULE TYPE: genomic DNA (iii) HYPOTHETICAL: no (xi) SEQUENCE DESCRIPTION: SEQ ID NO:32:

AATAAAAGCT GGCACTTGGC TTC                                           23

( 2 ) INFORMATION FOR SEQ ID NO:33:

( i ) SEQUENCE CHARACTERISTICS:
        ( A ) LENGTH: 19 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:33:

AATAAAAGCT GGCACTTGG    19

( 2 ) INFORMATION FOR SEQ ID NO:34:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:34:

AATAAAAGCT GGCACTTGGC TTCC    24

( 2 ) INFORMATION FOR SEQ ID NO:35:

( i ) SEQUENCE CHARACTERISTICS:
        ( A ) LENGTH: 34 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:35:

AATAAAAGCT GGCACTTGGC TTCCGCTTGT CTCT    34

( 2 ) INFORMATION FOR SEQ ID NO:36:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:36:

AATAAAAGCT GGCACTTGGC TTCCGCTTGT CTCTT    35

( 2 ) INFORMATION FOR SEQ ID NO:37:

( i ) SEQUENCE CHARACTERISTICS:
        ( A ) LENGTH: 148 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:37:

| | | |
|---|---|---|
| GAAGTGCCCC TTCTCCAGGA TCAAGGAACT GGGGCGGGGG GTGTTTCCTG | | 50 |
| GACCCCAGTC CTCCGAATCA GCTCCTAGAG TGGAACCAGG AAGGATTCTG | | 100 |
| GAGCCACAGA AGATAGACAG ATG GTAAGTCCCC TTTTGGAGTC AGAGG | | 148 |
| Met | | |

( 2 ) INFORMATION FOR SEQ ID NO:38:

( i ) SEQUENCE CHARACTERISTICS:
        ( A ) LENGTH: 128 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:38:

```
CTCCTTCTCC CTCCACTCAC TTCAG GAA GGT GGG GAC CAA AGT GAG GAA         49
                            Glu Gly Gly Asp Gln Ser Glu Glu
                             1               5

GAG CCG AGG GAA CGC AGC CAG GCA GGT GGA ATG GGA ACT CTC TGG         94
Glu Pro Arg Glu Arg Ser Gln Ala Gly Gly Met Gly Thr Leu Trp
     10              15              20

AGC CAA GAG GTAAGTGGCC TCCTCTCCTG GGTCT                            128
Ser Gln Glu
     25
```

( 2 ) INFORMATION FOR SEQ ID NO:39:

( i ) SEQUENCE CHARACTERISTICS:
        ( A ) LENGTH: 207 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:39:

```
TTTCACCTCT TGGTTCCTCC CACAG AGC ACT CCA GAA GAG AGG CTG CCC         49
                            Ser Thr Pro Glu Glu Arg Leu Pro
                             1               5

GTG GAA GGG AGC AGG CCA TGG GCA GTG GCC AGG CGG GTG CTG ACA         94
Val Glu Gly Ser Arg Pro Trp Ala Val Ala Arg Arg Val Leu Thr
     10              15              20

GCT ATC CTG ATT TTG GGC CTG CTC CTT TGT TTT TCT CTC CTT TGT        139
Ala Ile Leu Ile Leu Gly Leu Leu Leu Cys Phe Ser Leu Leu Cys
     25              30              35

TTT TCT GTG CTT TTG TTC TAC AAC TTC CAG AAC TGT GGC CCT C          182
Phe Ser Val Leu Leu Phe Tyr Asn Phe Gln Asn Cys Gly Pro
     40              45              50

GTAAGCAAGA TCCCAGACCC CCCAA                                        207
```

( 2 ) INFORMATION FOR SEQ ID NO:40:

( i ) SEQUENCE CHARACTERISTICS:
        ( A ) LENGTH: 227 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:40:

```
CCCAGCTCTG AGCTTTTCCC CACAG GC CCC TGT GAG ACA TCT GTG TGT              48
                               Arg Pro Cys Glu Thr Ser Val Cys
                                1                 5

TTG GAT CTC CGG GAT CAT TAC CTG GCC TCT GGG AAC ACA AGT GTG              93
Leu Asp Leu Arg Asp His Tyr Leu Ala Ser Gly Asn Thr Ser Val
     10              15                          20

GCC CCC TGC ACC GAC TTC TTC AGC TTT GCC TGT GGA AGG GCC AAA             138
Ala Pro Cys Thr Asp Phe Phe Ser Phe Ala Cys Gly Arg Ala Lys
     25              30                          35

GAG ACC AAT AAT TCT TTT CAG GAG CTT GCC ACA AAG AAC AAA AAC             183
Glu Thr Asn Asn Ser Phe Gln Glu Leu Ala Thr Lys Asn Lys Asn
     40              45                          50

CGA CTT CGG AGA ATA CTG G GTGAGGAAAG CAGGGTGGAA GATGC                   227
Arg Leu Arg Arg Ile Leu
     55
```

( 2 ) INFORMATION FOR SEQ ID NO:41:

( i ) SEQUENCE CHARACTERISTICS:
        ( A ) LENGTH: 181 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:41:

```
TTTAGTCCTC ACTCCCATGC TTCCTTTCTA G AG GTC CAG AAT TCC TGG                48
                                    Glu Val Gln Asn Ser Trp
                                     1                 5

CAC CCA GGC TCT GGG GAG GAG AAA GCC TTC CAG TTC TAC AAC TCC              93
His Pro Gly Ser Gly Glu Glu Lys Ala Phe Gln Phe Tyr Asn Ser
         10              15                          20

TGC ATG GAT ACA CTT GCC ATT GAA GCT GCA GGG ACT GGT CCC CTC             138
Cys Met Asp Thr Leu Ala Ile Glu Ala Ala Gly Thr Gly Pro Leu
         25              30                          35

AGA CAA GTT ATT GAG GAG GTGAGAAAAG TTGGGATATT AACTT                     181
Arg Gln Val Ile Glu Glu
         40
```

( 2 ) INFORMATION FOR SEQ ID NO:42:

( i ) SEQUENCE CHARACTERISTICS:
        ( A ) LENGTH: 197 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:42:

```
TCAGCCCCCT CTCTCTCCTT TAAAG CTT GGA GGC TGG CGC ATC TCT GGT              49
                               Leu Gly Gly Trp Arg Ile Ser Gly
                                1                 5

AAA TGG ACT TCC TTA AAC TTT AAC CGA ACG CTG AGA CTT CTG ATG              94
Lys Trp Thr Ser Leu Asn Phe Asn Arg Thr Leu Arg Leu Leu Met
     10              15                          20

AGT CAG TAT GGC CAT TTC CCT TTC TTC AGA GCC TAC CTA GGA CCT             139
Ser Gln Tyr Gly His Phe Pro Phe Phe Arg Ala Tyr Leu Gly Pro
```

```
                25                      30                         35
CAT  CCT  GCC  TCT  CCA  CAC  ACA  CCA  GTC  ATC  CAG  GTGAGGGATG                          182
His  Pro  Ala  Ser  Pro  His  Thr  Pro  Val  Ile  Gln
         40                      45

CACTGGCGAA GACAC                                                                            197
```

( 2 ) INFORMATION FOR SEQ ID NO:43:

( i ) SEQUENCE CHARACTERISTICS:
        ( A ) LENGTH: 113 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:43:

```
TCTCTCCAGT  CTCTCTTGTG  CCCAG  ATA  GAC  CAG  CCA  GAG  TTT  GAT  GTT              49
                                Ile  Asp  Gln  Pro  Glu  Phe  Asp  Val
                                 1                    5

CCC  CTC  AAG  CAA  GAT  CAA  GAA  CAG  AAG  ATC  TAT  GCC  CAG  GTAAG             93
Pro  Leu  Lys  Gln  Asp  Gln  Glu  Gln  Lys  Ile  Tyr  Ala  Gln
         10                      15                      20

ATGGCACATG GACAAAGGCC                                                              113
```

( 2 ) INFORMATION FOR SEQ ID NO:44:

( i ) SEQUENCE CHARACTERISTICS:
        ( A ) LENGTH: 239 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:44:

```
TGTGACTGAC  ATTTCCTTCC  TCCAG  ATC  TTT  CGG  GAA  TAC  CTG  ACT  TAC              49
                                Ile  Phe  Arg  Glu  Tyr  Leu  Thr  Tyr
                                 1                    5

CTG  AAT  CAG  CTG  GGA  ACC  TTG  CTG  GGA  GGA  GAC  CCA  AGC  AAG  GTG          94
Leu  Asn  Gln  Leu  Gly  Thr  Leu  Leu  Gly  Gly  Asp  Pro  Ser  Lys  Val
         10                      15                      20

CAA  GAA  CAC  TCT  TCC  TTG  TCA  ATC  TCC  ATC  ACT  TCA  CGG  CTG  TTC          139
Gln  Glu  His  Ser  Ser  Leu  Ser  Ile  Ser  Ile  Thr  Ser  Arg  Leu  Phe
         25                      30                      35

CAG  TTT  CTG  AGG  CCC  CTG  GAG  CAG  CGG  CGG  GCA  CAG  GGC  AAG  CTC          184
Gln  Phe  Leu  Arg  Pro  Leu  Glu  Gln  Arg  Arg  Ala  Gln  Gly  Lys  Leu
         40                      45                      50

TTC  CAG  ATG  GTC  ACT  ATC  GAC  CAG  CTC  AAG  GTGCCTGGAA                       224
Phe  Gln  Met  Val  Thr  Ile  Asp  Gln  Leu  Lys
         55                      60

CTGGGGGGCA GAAGA                                                                   239
```

( 2 ) INFORMATION FOR SEQ ID NO:45:

( i ) SEQUENCE CHARACTERISTICS:
        ( A ) LENGTH: 199 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:45:

| | | | | | | | | | | | | |
|---|---|---|---|---|---|---|---|---|---|---|---|---|
| CTCAGCTTTG | TGTCCCTCCT | CTAAG | GAA | ATG | GCC | CCC | GCC | ATC | GAC | TGG | | 49 |
| | | | Glu<br>1 | Met | Ala | Pro | Ala<br>5 | Ile | Asp | Trp | | |

| | | | | | | | | | | | |
|---|---|---|---|---|---|---|---|---|---|---|---|
| TTG | TCC | TGC | TTG | CAA | GCG | ACA | TTC | ACA | CCG | ATG | TCC | CTG | AGC | CCT | 94 |
| Leu | Ser | Cys | Leu | Gln | Ala | Thr | Phe | Thr | Pro | Met | Ser | Leu | Ser | Pro | |
| | 10 | | | | 15 | | | | | 20 | | | | | |

| TCT | CAG | TCC | CTC | GTG | GTC | CAT | GAC | GTG | GAA | TAT | TTG | AAA | AAC | ATG | 139 |
|---|---|---|---|---|---|---|---|---|---|---|---|---|---|---|---|
| Ser | Gln | Ser | Leu | Val | Val | His | Asp | Val | Glu | Tyr | Leu | Lys | Asn | Met | |
| 25 | | | | | 30 | | | | | 35 | | | | | |

| TCA | CAA | CTG | GTG | GAG | GAG | ATG | CTG | CTA | AAG | CAG | AG | GTTCGCCGCA | 184 |
|---|---|---|---|---|---|---|---|---|---|---|---|---|---|
| Ser | Gln | Leu | Val | Glu | Glu | Met | Leu | Leu | Lys | Gln | Arg | | |
| 40 | | | | | 45 | | | | | 50 | | | |

GGTGGGATTG GGGAG                                                                                              199

( 2 ) INFORMATION FOR SEQ ID NO:46:

( i ) SEQUENCE CHARACTERISTICS:
        ( A ) LENGTH: 180 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:46:

| GTGTGGGTCT | CTTTTGTCTC | CATAG | G | GAC | TTT | CTG | CAG | AGC | CAC | ATG | 47 |
|---|---|---|---|---|---|---|---|---|---|---|---|
| | | | | Asp<br>1 | Phe | Leu | Gln | Ser<br>5 | His | Met | |

| ATC | TTA | GGG | CTG | GTG | GTG | ACC | CTT | TCT | CCA | GCC | CTG | GAC | AGT | CAA | 92 |
|---|---|---|---|---|---|---|---|---|---|---|---|---|---|---|---|
| Ile | Leu | Gly | Leu | Val | Val | Thr | Leu | Ser | Pro | Ala | Leu | Asp | Ser | Gln | |
| | 10 | | | | 15 | | | | | 20 | | | | | |

| TTC | CAG | GAG | GCA | CGC | AGA | AAG | CTC | AGC | CAG | AAA | CTG | CGG | GAA | CTG | 137 |
|---|---|---|---|---|---|---|---|---|---|---|---|---|---|---|---|
| Phe | Gln | Glu | Ala | Arg | Arg | Lys | Leu | Ser | Gln | Lys | Leu | Arg | Glu | Leu | |
| | 25 | | | | 30 | | | | | 35 | | | | | |

| ACA | GAG | CAA | CCA | CCC | ATG | GTGAGGAGAG | GAGCGGGTGT | ATTTG | 180 |
|---|---|---|---|---|---|---|---|---|---|
| Thr | Glu | Gln | Pro | Pro | Met | | | | |
| | | 40 | | | | | | | |

( 2 ) INFORMATION FOR SEQ ID NO:47:

( i ) SEQUENCE CHARACTERISTICS:
        ( A ) LENGTH: 161 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:47:

| ACTCATTCCA | GCTTTGTCTC | CATAG | CCT | GCC | CGC | CCA | CGA | TGG | ATG | AAG | 49 |
|---|---|---|---|---|---|---|---|---|---|---|---|
| | | | Pro<br>1 | Ala | Arg | Pro | Arg<br>5 | Trp | Met | Lys | |

| TGC | GTG | GAG | GAG | ACA | GGC | ACG | TTC | TTC | GAG | CCC | ACG | CTG | GCG | GCT | 94 |
|---|---|---|---|---|---|---|---|---|---|---|---|---|---|---|---|
| Cys | Val | Glu | Glu | Thr | Gly | Thr | Phe | Phe | Glu | Pro | Thr | Leu | Ala | Ala | |
| | 10 | | | | 15 | | | | | 20 | | | | | |

| TTG | TTT | GTT | CGT | GAG | GCC | TTT | GGC | CCG | AGC | ACC | CGA | AGT | GCT | 136 |
|---|---|---|---|---|---|---|---|---|---|---|---|---|---|---|
| Leu | Phe | Val | Arg | Glu | Ala | Phe | Gly | Pro | Ser | Thr | Arg | Ser | Ala | |
| | 25 | | | | 30 | | | | | 35 | | | | |

```
GTATGTGAGA  GCTCTTCCCA  GCCCA                                                           161
```

( 2 ) INFORMATION FOR SEQ ID NO:48:

( i ) SEQUENCE CHARACTERISTICS:
        ( A ) LENGTH: 149 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:48:

```
CTGTCCCTGG  ACCTCACTCC  CACAG GCC ATG AAA TTA TTC ACT GCG ATC            49
                              Ala Met Lys Leu Phe Thr Ala Ile
                              1               5

CGG GAT GCC CTC ATC ACT CGC CTC AGA AAC CTT CCC TGG ATG AAT              94
Arg Asp Ala Leu Ile Thr Arg Leu Arg Asn Leu Pro Trp Met Asn
    10              15              20

GAG GAG ACC CAG AAC ATG GCC CAG GAC AAG GTCAGGCCAG                       134
Glu Glu Thr Gln Asn Met Ala Gln Asp Lys
    25              30

GCGTCCTGGC  TGGTG                                                        149
```

( 2 ) INFORMATION FOR SEQ ID NO:49:

( i ) SEQUENCE CHARACTERISTICS:
        ( A ) LENGTH: 128 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:49:

```
TAGCCTCTTC  TGTGTCTCTC  TCCAG GTT GCT CAA CTG CAG GTG GAG ATG            49
                              Val Ala Gln Leu Gln Val Glu Met
                              1               5

GGG GCT TCA GAA TGG GCC CTG AAG CCA GAG CTG GCC CGA CAA GAA              94
Gly Ala Ser Glu Trp Ala Leu Lys Pro Glu Leu Ala Arg Gln Glu
    10              15              20

TAC AAC GAT GTGGGTCCCT GTGTTTTCCA GCTCC                                  128
Tyr Asn Asp
    25
```

( 2 ) INFORMATION FOR SEQ ID NO:50:

( i ) SEQUENCE CHARACTERISTICS:
        ( A ) LENGTH: 151 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:50:

```
AAGTCACCTC  CTGCCTCTTC  CCCAG ATA CAG CTT GGA TCG AGC TTC CTG            49
                              Ile Gln Leu Gly Ser Ser Phe Leu
                              1               5

CAG TCT GTC CTG AGC TGT GTC CGG TCC CTC CGA GCT AGA ATT GTC              94
Gln Ser Val Leu Ser Cys Val Arg Ser Leu Arg Ala Arg Ile Val
```

```
                   10                    1 5                         2 5
CAG  AGC  TTC  TTG  CAG  CCT  CAC  CCC  CAA  CAC  AG GTATGACAGC AGGGG         141
Gln  Ser  Phe  Leu  Gln  Pro  His  Pro  Gln  His  Arg
          30                      35

AGACACAGGC                                                                     151
```

( 2 ) INFORMATION FOR SEQ ID NO:51:

( i ) SEQUENCE CHARACTERISTICS:
        ( A ) LENGTH: 161 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:51:

```
GAGTTCACAT GTCCTCTTCC CACAG G  TGG  AAG  GTG  TCC  CCT  TGG  GAC              47
                              Trp  Lys  Val  Ser  Pro  Trp  Asp
                               1                    5

GTC  AAT  GCT  TAC  TAT  TCG  GTA  TCT  GAC  CAT  GTG  GTA  GTC  TTT  CCA     92
Val  Asn  Ala  Tyr  Tyr  Ser  Val  Ser  Asp  His  Val  Val  Val  Phe  Pro
          10                       15                           20

GCT  GGA  CTC  CTC  CAA  CCC  CCA  TTC  TTC  CAC  CCT  GGC  TAT  CCC  AG     136
Ala  Gly  Leu  Leu  Gln  Pro  Pro  Phe  Phe  His  Pro  Gly  Tyr  Pro  Arg
          25                       30                           35

GTATGGGTCA CTCTGTAAGG GTAGG                                                   161
```

( 2 ) INFORMATION FOR SEQ ID NO:52:

( i ) SEQUENCE CHARACTERISTICS:
        ( A ) LENGTH: 118 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:52:

```
GTCAAATAAG CCCTTGTCTC CCTAG A  GCC  GTG  AAC  TTT  GGC  GCT  GCT              47
                              Ala  Val  Asn  Phe  Gly  Ala  Ala
                               1                    5

GGC  AGC  ATC  ATG  GCC  CAC  GAG  CTG  TTG  CAC  ATC  TTC  TAC  CAG  CTC     92
Gly  Ser  Ile  Met  Ala  His  Glu  Leu  Leu  His  Ile  Phe  Tyr  Gln  Leu
          10                       15                           20

T GTGGGTAACA GGGGCCACTG GGAGG                                                 118
```

( 2 ) INFORMATION FOR SEQ ID NO:53:

( i ) SEQUENCE CHARACTERISTICS:
        ( A ) LENGTH: 220 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:53:

```
TGTTCTCTTG TCCCATTTTC AACAG TA  CTG  CCT  GGG  GGC  TGC  CTC  GCC             48
                               Leu  Leu  Pro  Gly  Gly  Cys  Leu  Ala
                                1                    5
```

```
TGT GAC AAC CAT GCC CTC CAG GAA GCT CAC CTG TGC CTG AAG CGC        93
Lys Asp Asn His Ala Leu Gln Glu Ala His Leu Cys Leu Lys Arg
    10              15              20

CAT TAT GCT GCC TTT CCA TTA CCT AGC AGA ACC TCC TTC AAT GAC       138
His Tyr Ala Ala Phe Pro Leu Pro Ser Arg Thr Ser Phe Asn Asp
    25              30              35

TCC CTC ACA TTC TTA GAG AAT GCT GCA GAC GTT GGG GGG CTA GCC       183
Ser Leu Thr Phe Leu Glu Asn Ala Ala Asp Val Gly Gly Leu Ala
    40              45              50

ATC GCG CTG CAG GTATGCAAGT GTCAAGGGCC ACAGT                       220
Ile Ala Leu Gln
    55
```

( 2 ) INFORMATION FOR SEQ ID NO:54:

( i ) SEQUENCE CHARACTERISTICS:
        ( A ) LENGTH: 146 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:54:

```
CCCTTCTCTA CCCACCCCTA CCCAG GCA TAC AGC AAG AGG CTG TTA CGG        49
                            Ala Tyr Ser Lys Arg Leu Leu Arg
                            1               5

CAC CAT GGG GAG ACT GTC CTG CCC AGC CTG GAC CTC AGC CCC CAG        94
His His Gly Glu Thr Val Leu Pro Ser Leu Asp Leu Ser Pro Gln
        10              15              20

CAG ATC TTC TTT CGA AGC TAT GCC CAG GTAGGCAGCG GCCACCTCCC         141
Gln Ile Phe Phe Arg Ser Tyr Ala Gln
    25              30

GCCAC                                                             146
```

( 2 ) INFORMATION FOR SEQ ID NO:55:

( i ) SEQUENCE CHARACTERISTICS:
        ( A ) LENGTH: 313 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:55:

```
TTCAATAACC TCTCTTCCTG CTCAG GTG ATG TGT AGG AAG CCC AGC CCC        49
                            Val Met Cys Arg Lys Pro Ser Pro
                            1               5

CAG GAC TCT CAC GAC ACT CAC AGC CCT CCA CAC CTC CGA GTC CAC        94
Gln Asp Ser His Asp Thr His Ser Pro Pro His Leu Arg Val His
        10              15              20

GGG CCC CTC AGC AGC ACC CCA GCC TTT GCC AGG TAT TTC CGC TGT       139
Gly Pro Leu Ser Ser Thr Pro Ala Phe Ala Arg Tyr Phe Arg Cys
    25              30              35

GCA CGT GGT GCT CTC TTG AAC CCC TCC AGC CGC TGC CAG CTC TGG       184
Ala Arg Gly Ala Leu Leu Asn Pro Ser Ser Arg Cys Gln Leu Trp
    40              45              50

TAACTTGGTT ACCAAAGATG CCACAGCACA GAAATATCGA CCAACACCTC             234

CCTGGTCACA TCCATGGAAT CAGAGCAAGA TTTCCTTTCT GCTTCTGTTC             284
```

CAAAAATAAA AGCTGGCACT TGGCTTCCG                                                              313

( 2 ) INFORMATION FOR SEQ ID NO:56:

( i ) SEQUENCE CHARACTERISTICS:
        ( A ) LENGTH: 327 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:56:

```
GTCACAGTGC AAGACAAAAG GAGCAGACCA AGGGCAAGAT TGCTTGGGGA        50
GTGAAGACTC CCTCCCTCTT CTCCCCTGAG AAGCTGAGAT AAAGGGGGAG       100
GAGAAGCCTG GGTGCCCCCC ACTGATAAGC AGGCTCCACC CAGAGGCCAG       150
TCCTGTGTGT CTGGGGACAA GGCGAAAGAG CAGCAGAAGT GCCCCTTCTC       200
CAGGATCAAG GAACTGGGGC GGGGGGTGTT TCCTGGACCC CAGTCCTCCG       250
AATCAGCTCC TAGAGTGGAA CCAGGAAGGA TTCTGGAGCC ACAGAAGATA       300
GACAGAGTGT AAGTCCCCTT TTGGAGT                                327
```

( 2 ) INFORMATION FOR SEQ ID NO:57:

( i ) SEQUENCE CHARACTERISTICS:
        ( A ) LENGTH: 45 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:57:

```
TGG ACT TCC TTA AAC TTT AAC CGA ACG CTG AGA CTT CTG ATG AGT       45
Trp Thr Ser Leu Asn Phe Asn Arg Thr Leu Arg Leu Leu Met Ser
1               5                   10                  15
```

( 2 ) INFORMATION FOR SEQ ID NO:58:

( i ) SEQUENCE CHARACTERISTICS:
        ( A ) LENGTH: 45 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:58:

```
TGG ACT TCC TTA AAC TTT AAC CGA ATG CTG AGA CTT CTG ATG AGT       45
Trp Thr Ser Leu Asn Phe Asn Arg Met Leu Arg Leu Leu Met Ser
1               5                   10                  15
```

( 2 ) INFORMATION FOR SEQ ID NO:59:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide (v) FRAGMENT TYPE: internal fragment (xi) SEQUENCE DESCRIPTION: SEQ ID NO:59:

His Glu Leu Leu His
1               5

(2) INFORMATION FOR SEQ ID NO:60:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal fragment (ix) FEATURE:
        (A) NAME/KEY: variable residues
        (B) LOCATION: 3-4
        (C) OTHER INFORMATION: /note= consensus sequence found
            in active sites of zinc neutral peptidases (xi) SEQUENCE DESCRIPTION: SEQ ID NO:60:

His Glu Xaa Xaa His
1               5